United States Patent
Goldfarb et al.

(10) Patent No.: US 11,883,304 B2
(45) Date of Patent: Jan. 30, 2024

(54) PROSTHETIC KNEE WITH SWING ASSIST

(71) Applicant: Vanderbilt University, Nashville, TN (US)

(72) Inventors: Michael Goldfarb, Franklin, TN (US); Almaskhan Baimyshev, Nashville, TN (US); Harrison Bartlett, Nashville, TN (US); Jantzen Lee, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 18/046,447

(22) Filed: Oct. 13, 2022

(65) Prior Publication Data
US 2023/0055765 A1 Feb. 23, 2023

Related U.S. Application Data

(63) Continuation of application No. 16/961,723, filed as application No. PCT/US2019/015269 on Jan. 25, 2019, now Pat. No. 11,471,306.
(Continued)

(51) Int. Cl.
| | |
|---|---|
| *A61F 2/64* | (2006.01) |
| *A61F 2/70* | (2006.01) |
| *A61F 2/50* | (2006.01) |
| *A61F 2/76* | (2006.01) |
| *A61F 2/74* | (2006.01) |

(52) U.S. Cl.
CPC ............... *A61F 2/644* (2013.01); *A61F 2/70* (2013.01); *A61F 2/74* (2021.08); *A61F 2/741* (2021.08);
(Continued)

(58) Field of Classification Search
CPC .. A61F 2/644; A61F 2/70; A61F 2/741; A61F 2/74; A61F 2/748
See application file for complete search history.

(56) References Cited

U.S. PATENT DOCUMENTS

| | | |
|---|---|---|
| 5,545,233 A | 8/1996 | Fitzlaff |
| 5,704,945 A | 1/1998 | Wagner |

(Continued)

FOREIGN PATENT DOCUMENTS

| | | |
|---|---|---|
| CA | 2772620 A1 | 3/2011 |

OTHER PUBLICATIONS

International Search Report and Written Opinion in International Application No. PCT/US2019/015269, dated Apr. 19, 2019 (10 pages).

(Continued)

*Primary Examiner* — Jerrah Edwards
*Assistant Examiner* — Maximilian Tobias Spencer
(74) *Attorney, Agent, or Firm* — Nixon Peabody LLP

(57) ABSTRACT

The present disclosure provides for a device and method of control for an artificial prosthetic knee. A prosthetic knee according to the present disclosure relies on strictly passive means of providing support during weight bearing and supplements a resistive swing-phase mechanism with a small powered actuator. This actuator adds power to the knee, exclusively during swing phase, to improve swing-phase behavior. In particular, the knee still relies on the resistive swing-phase mechanism to provide nominal swing-phase knee motion, but supplements that motion as needed with the small powered actuator.

9 Claims, 23 Drawing Sheets

Related U.S. Application Data

(60) Provisional application No. 62/775,651, filed on Dec. 5, 2018, provisional application No. 62/621,917, filed on Jan. 25, 2018.

(52) U.S. Cl.
CPC ....... *A61F 2/748* (2021.08); *A61F 2002/5006* (2013.01); *A61F 2002/5033* (2013.01); *A61F 2002/5035* (2013.01); *A61F 2002/701* (2013.01); *A61F 2002/704* (2013.01); *A61F 2002/764* (2013.01); *A61F 2002/7625* (2013.01); *A61F 2002/7635* (2013.01)

(56) References Cited

U.S. PATENT DOCUMENTS

| | | | |
|---|---|---|---|
| 7,588,604 | B2 | 9/2009 | Okuda |
| 8,231,688 | B2 | 7/2012 | Fairbanks |
| 2004/0249267 | A1 | 12/2004 | Meyers |
| 2010/0023133 | A1 | 1/2010 | Fairbanks |
| 2011/0098828 | A1 | 4/2011 | Balboni |
| 2013/0150980 | A1* | 6/2013 | Swift ................ A61F 2/70 623/24 |
| 2013/0310949 | A1 | 11/2013 | Geyer |
| 2016/0158029 | A1 | 6/2016 | Kuiken |
| 2017/0151069 | A1 | 6/2017 | Geyer |

OTHER PUBLICATIONS

Park, J. et al., "Design and control of a prosthetic leg for above-knee amputees operated in semi-active and active modes," Smart Mater. Struct. 25 085009, Jul. 11, 2016 (13 pages).

Supplementary European Search Report in European Patent Application No. EP 19744587.7, dated Sep. 1, 2021 (14 pages).

Extended European Search Report in European Patent Application No. EP 19744587.7, dated Dec. 3, 2021 (13 pages).

\* cited by examiner

PROSTHETIC KNEE WITH SWING ASSIST

CROSS REFERENCE TO RELATED APPLICATIONS

This application is a continuation of U.S. patent application Ser. No. 16/961,723 filed Jul. 13, 2020, which has been allowed; U.S. patent application Ser. No. 16/961,723 is a U.S. National Stage Entry of International Application No. PCT/US2019/015269, filed Jan. 25, 2019, which claims priority under 35 U.S.C. § 119 to U.S. Provisional Application No. 62/621,917 entitled "PROSTHETIC KNEE WITH SWING ASSIST," filed on Jan. 25, 2018 and also claims priority under 35 U.S.C. § 119 to U.S. Provisional Application No. 62/775,651 entitled "DESIGN OF A SEMI-POWERED STANCE-CONTROL SWING-ASSIST TRANSFEMORAL PROSTHESIS," filed on Dec. 5, 2018, in which all of these applications are hereby incorporated by reference in their entirety.

STATEMENT OF GOVERNMENT SUPPORT

This invention was made with government support under grant number HD088959 awarded by the National Institutes of Health. The government has certain rights in the invention.

FIELD

The present disclosure relates to an artificial prosthetic knee with passive support during a weight-bearing phase and powered assistance during a swing phase.

BACKGROUND

A conventional knee prosthesis employs a high-resistance mechanism to provide support during the stance phase of gait (i.e., during weight bearing), and a low-resistance mechanism that provides appropriate swing-phase motion in response to user thigh input (i.e, swinging the thigh forward). Such knee prostheses provide two essential functions, which correspond to the two major phases of gait (the stance phase and the swing phase). During the stance phase of gait, when a user bears weight on the prosthesis, the knee prosthesis supports the weight of the user and prevents the knee from buckling while loaded. During the swing phase of gait, when a user is swinging the prosthetic leg forward, the knee prosthesis initially allows the knee to flex and subsequently to extend, which allows the prosthetic foot to clear the ground as it is brought forward for the next step, and allows the prosthetic knee to return to full extension in preparation for the subsequent weight-bearing stance phase.

Conventional hyperextension stops are used in conventional prostheses to prevent the knee from extending substantially beyond a fully-extended configuration. Such a hyperextension stop is engaged during the stance phase by the user via a combination of user hip torque and ground reaction force. Conventional hyperextension stops, however, do not provide robust stance knee stability; a slight perturbation can result in rapid knee buckling in the flexion direction.

In order to improve the stance-phase robustness of a prosthetic knee joint with a hyperextension stop, polycentric knee joints have been employed in place of knee joints designed with a single knee joint axis. In a polycentric knee joint, the single knee joint axis is replaced by a linkage (e.g., a four-bar linkage), designed with an instant center of rotation that moves posterior to the anatomical knee joint as the knee nears full extension. When weight is placed on the prosthesis, the ground reaction vector passes anterior to the instant center of rotation of the polycentric linkage, thus enhancing the passive stability associated with the hyperextension stop.

Although a polycentric knee increases the robustness of knee stability relative to a single-axis knee, a polycentric knee requires the knee be fully extended to be stable. In many cases, however, a user may want the stance knee to be stable or to provide a high level of resistance in a substantially flexed configuration while weight bearing. Examples of this "stance knee yielding" behavior include stair descent, slope descent, and stand-to-sit transitions. In order to improve the robustness of knee stability during stance phase, and also to allow stance knee yielding during activities such as slope and stair descent, conventional "stance control" prostheses employ mechanisms that support stance knee yielding functionality. In nearly all cases, these conventional stance control mechanisms employ a modulated dissipater (e.g., a hydraulic damper with a controllable valve) that provides substantial resistance at the knee joint during the weight-bearing phase of gait (i.e., during stance). In some conventional devices, the modulated dissipater is engaged when the device detects the amount of weight a user has on the leg, either mechanically or via an electrical load sensor. In some conventional devices, the knee stability mechanism is engaged based on configuration, such as when the knee is nearly extended and the angle of the device relative to gravity indicates a configuration near heel strike. Such modulated dissipaters can be employed with either a single-axis or polycentric knee design. In all cases of conventional prostheses, the modulated dissipater must also detect the onset of the swing phase, because the stance-phase resistance provided by the modulated dissipater must be dramatically reduced in order to allow for a suitable swing-phase motion of the knee. Such detection of the onset of swing can be either through mechanical or electronic sensing.

During swing phase, the prosthetic knee is intended to provide an appropriate movement of the knee during swing, such that a user can swing the prosthetic foot forward following stance phase, clearing the ground and returning the knee to full extension ahead of the subsequent stance phase. In a conventional knee prosthesis, the mechanical power that generates swing phase is provided by the user via his or her hip, which generates corresponding rotational motion at the knee via inertial coupling between the thigh and shank. Specifically, accelerating the thigh forward generates flexion of the prosthetic knee joint, while subsequently decelerating the thigh generates knee extension. Because the power for knee movement is supplied by the hip, mechanisms in a conventional prosthetic knee that "control" swing motion consist of resistive elements (e.g., hydraulic or pneumatic damping elements) that slightly resist and smooth out the initial flexion and subsequent extension of the prosthetic knee resulting from thigh acceleration and deceleration during prosthetic swing phase. Without such resistive elements, the knee would flex excessively during the flexion portion of swing phase, and extend too quickly during the subsequent extension phase, resulting in high angular velocity of the knee joint in late swing. Such undamped knee movement results in unnatural foot motion during swing, including movement that is not well-synchronized with gait. The high angular velocity of the knee in terminal swing results in a high impact at full knee extension (against the hyperextension stops) that can be damaging to the device and uncomfortable to the user; this high impact consequently makes the transition into stance knee stability more challenging and unsafe. This impact is called "terminal impact," and is undesirable in a prosthetic knee.

In some devices, the swing resistance in the knee is provided by pneumatic or hydraulic damping means. Such fluid-based damping can provide a more natural appearance of motion relative to dry frictional means. Although the inertial coupling between the thigh and shank segments naturally results in initial flexion and subsequent extension of the knee during swing, many knee prostheses additionally employ an "extension aid," which is typically a spring configured such that the resting configuration of the knee is in the fully extended state. With such an extension aid, the amount of knee flexion during swing will be decreased relative to without it (i.e., the extension spring opposes flexion). In exchange, however, the knee is more assured of reaching full extension in terminal swing, which is essential for stance-phase stability and functionality. As such, a spring-based extension aid reduces the amount of flexion during swing phase in exchange for greater assurance of extension in terminal swing.

In such devices, it is important to understand that the mechanisms associated with producing swing-phase motion—typically a light fluid damper and an extension spring—are passive elements that collectively provide an approximate movement, in an open-loop manner, in response to hip and thigh movement by the user. Although this conventional method provides appropriate nominal behavior during the swing phase of walking, it has substantial deficiencies. First, conventional knees do not provide the ideal magnitude of knee flexion during swing phase; knee flexion in conventional prostheses is roughly invariant as a function of walking cadence. The inertial forces that couple knee motion to hip motion, however, are highly variable with walking cadence in biological leg movement. Frictional knees of conventional prostheses, which generally provide rate-independent resistance, are unable to adjust resistance appropriately across walking cadence, and thus generally confine an individual to a single cadence.

Knees with fluidic damping, such as hydraulic or pneumatic, provide a rate-dependent resistance, and therefore offer improved accommodation of variable cadence. However, conventional knees with fluidic damping generally still provide compromised knee movement as a function of walking cadence relative to healthy movement, especially at very slow or very fast walking cadences (i.e., unlike the desired behavior, knee flexion in these prostheses is substantially reduced at slow speeds and increased at high speeds). Further, hydraulic devices in particular are substantially affected by environmental temperature, due to the increase in fluid viscosity at low temperatures. As such, swing-phase behavior changes substantially with temperature. Therefore, conventional resistive mechanisms (frictional and fluid) are generally unable to provide desired knee motion across a wide range of walking speeds and environmental conditions.

Additionally, conventional resistive devices of existing prostheses are compromised in providing appropriate swing knee motion for activities other than level walking. For example, when walking up slopes, gravity removes energy from the swinging leg, thus altering the swing-phase mechanics. When walking down stairs, the movement can be much slower, which removes much of the inertial coupling from the thigh and shank, and lessens the user's ability to effect knee motion. The knee movement provided by passive damping, which is tuned nominally to provide appropriate swing during walking, also provides compromised knee movement when engaging in other activities, such as when ascending or descending stairs.

Finally, since the swing-phase knee character in such conventional prostheses is resistive, the knee is unable to respond robustly to perturbations in the swing, such as those caused by scuffing between the foot and ground during swing, or by stumble. In such cases, passive knee mechanisms cannot supply the reactive power required to appropriately respond to the stumble or scuff perturbation, in which case the knee is unlikely to achieve full extension, and as a result the likelihood of the user falling is substantially increased. This is a significant problem in this population—studies show that individuals with transfemoral amputation are 200 times more likely to fall, relative to age-matched healthy individuals.

Some conventional prostheses provide for an electric motor and mechanical transmission, powered by a battery, to provide both stance-phase stability and swing-phase movement. Since swing phase is powered rather than resistive in these devices, powered knees are able to actively drive swing-phase motion, and therefore are able to address the aforementioned deficiencies of swing-phase motion in resistive knee prostheses. Since the knee torques associated with providing stance phase stability are substantially larger than the knee torques associated with swing phase movement, however, the size and weight of the motor and transmission of powered knee prostheses is dictated by the (much more demanding) stance phase requirements. Since powered devices (e.g., motor, transmission, and battery) are known to have substantially lower torque and power densities relative to hydraulic devices, a powered knee prosthesis that can provide the same stance-phase knee torque and power as a hydraulic device will be substantially larger and heavier than the hydraulic device. In powered prostheses intended to provide stance-phase support, swing-phase deficiencies are addressed, but at the expense of considerable added weight in the knee prosthesis, which is a substantially liability in such devices.

SUMMARY

The various examples of the present disclosure are directed towards knee prosthesis. A first embodiment of the knee prosthesis includes a shank link, a thigh link, at least one resistive control element, at least one powered control element, at least one sensor, and a controller. The thigh link is rotatably coupled to the shank link. The at least one resistive control element can apply two levels of resistance to resist rotation of the thigh link relative to the shank link. The at least one powered control element is distinct and separate from the resistive control element. This powered control element is further configured to power rotation of the thigh link relative to the shank link. The controller can be coupled to the at least one sensor and can be configured to perform a series of tasks. The controller can receive sensor measurements from the at least one sensor. Based on the sensor measurements, the controller can determine a present state of the knee prosthesis. A present state can include any of a plurality of states, including, at least, a swing state and a stance state. The controller can also cause the at least one resistive control element to apply a first level of resistance when the knee prosthesis is in the swing state. The controller can also cause the at least one resistive control element to apply a second level of resistance when the knee prosthesis is in the stance state. The controller can also cause the at least one powered control element to power rotation when the knee prosthesis is in the swing state.

In some examples of the first embodiment, the at least one powered control element can apply a maximum torque on the knee prosthesis. This maximum torque is substantially smaller than a maximum torque applied on the knee prosthesis by the at least one resistive control element.

In some examples of the first embodiment, the controller can perform additional tasks. When the knee prosthesis is in a swing state, the controller can provide a desired swing knee motion trajectory. Based on this desired swing knee motion trajectory, the controller can determine a magnitude of the first level of resistance, which can provide this nominal desired motion, in the absence of perturbations or variation in environment conditions. The controller can further measure knee motion in the swing state and determine a knee motion error based on a difference between the desired swing knee motion trajectory and the measured knee motion. This difference could be caused by perturbations, or variations in activity or walking cadence, variation in environmental conditions, etc. In order to reduce or eliminate this error, the controller can provide a powered assistance from the at least one powered control element to the knee prosthesis to supplement the passive resistance of the at least one resistive control element. This powered assistance can reduce the knee motion error in the swing state, and can add power in small amounts when the addition of such power will result in a more consistent or desirable swing phase motion.

In some examples of the first embodiment, a peak knee flexion of the desired swing knee motion trajectory can be based on a measured walking cadence of a user.

A second embodiment of the present disclosure can provide for a shank link, a thigh link, at least one resistive control element, at least one powered control element, at least one sensor, and a controller. The thigh link can be rotatably coupled to the shank link. The at least one resistive control element can apply three levels of resistance to resist rotation of the thigh link relative to the shank link. The at least one powered control element is distinct and separate from the resistive control element. This powered control element is further configured to power rotation of the thigh link relative to the shank link. The controller can be coupled to the at least one sensor and can be configured to perform a series of tasks. The controller can receive sensor measurements from the at least one sensor. Based on the sensor measurements, the controller can determine a present state of the knee prosthesis. A present state can include any of a plurality of states, including at least, a swing state, a stance state, and a stair descent state. The controller can also cause the at least one resistive control element to apply a first level of resistance when the knee prosthesis is in the swing state. The controller can also cause the at least one resistive control element to apply a second level of resistance when the knee prosthesis is in the stance state. The controller can also cause the at least one resistive control element to apply a third level of resistance when the knee prosthesis is in the stair descent state. The controller can also cause the at least one powered control element to power rotation when the knee prosthesis is in the swing state.

In some examples of the second embodiment, the controller can perform additional tasks. When the knee prosthesis is in a swing state, the controller can provide a desired swing knee motion trajectory. Based on this desired swing knee motion trajectory, the controller can determine a magnitude of the first level of resistance. The controller can further measure knee motion in the swing state and determine a knee motion error based on a difference between the desired swing knee motion trajectory and the measured knee motion. The controller can additionally provide a powered assistance from the at least one powered control element to the knee prosthesis. This powered assistance can reduce the knee motion error in the swing state.

In some examples of the second embodiment, the plurality of states can further include a stair descent swing state. The controller can also perform additional tasks. When the knee prosthesis is in the stair descent swing state, the controller can provide a desired swing knee motion trajectory. Based on this desired swing knee motion trajectory, the controller can determine a magnitude of the first level of resistance. The controller can further measure knee motion in the stair descent swing state and determine a knee motion error based on a difference between the desired swing knee motion trajectory and the measured knee motion. The controller can additionally provide a powered assistance from the at least one powered control element to the knee prosthesis. This powered assistance can reduce the knee motion error in the stair descent swing state.

In some examples of the second embodiment, the plurality of states can further include a stair ascent swing state. The controller can also perform additional tasks. When the knee prosthesis is in the stair ascent swing state, the controller can provide a desired swing knee motion trajectory. The controller can further measure knee motion in the stair ascent swing state and determine a knee motion error based on a difference between the desired swing knee motion trajectory and the measured knee motion. The controller can additionally provide a powered assistance from the at least one powered control element to the knee prosthesis. This powered assistance can reduce the knee motion error in the stair ascent swing state.

In some examples of the second embodiment, the at least one resistive control element can include a hydraulic actuator cylinder. The hydraulic actuator cylinder can be coupled to the knee joint and can provide the first, second, and third levels of resistance. The levels of resistance can be provided based on hydraulic fluid flow through a hydraulic valve of the hydraulic actuator cylinder. The hydraulic fluid flow can be generated by knee joint rotation.

In some examples of the second embodiment, the hydraulic valve can include an orifice. The orifice can couple with a first, second, and/or third orifice opening. Each of the orifice openings provide one of the first, second, or third levels of resistance.

In some examples of the second embodiment, the at least one powered control element can include an electric motor. The electric motor can be coupled to the thigh link and the shank link through a power screw transmission. The power screw transmission can be located within a rod of the hydraulic cylinder.

In some examples of the second embodiment, the at least one powered control element can include an electric motor coupled to the thigh link and the shank link through a power screw transmission.

A third embodiment of the present disclosure can provide for a shank link, a thigh link, a polycentric knee joint, at least one powered control element, at least one sensor, and a controller. The thigh link can be rotatably coupled to the shank link. The polycentric knee joint can include an extension stop to substantially prevent the knee prosthesis from hyperextending. The powered control element is further configured to power rotation of the thigh link relative to the shank link. The controller can be coupled to the at least one sensor can be configured to perform a series of tasks. The controller can receive sensor measurements from the at least one sensor. Based on the sensor measurements, the controller can determine a present state of the knee prosthesis. A present state can include any of a plurality of states, including at least a swing state and a stance state. The controller can also cause the at least one powered control element to power rotation when the knee prosthesis is in the swing state. The polycentric knee joint can be further configured to provide a center of rotation of the thigh link relative to the shank link. This center of rotation can be substantially posterior to a ground reaction force vector when the present state is the stance state.

In some examples of the third embodiment, the at least one powered control element can apply a maximum torque on the knee prosthesis. This maximum torque can be substantially smaller than a maximum torque applied on the knee prosthesis by the polycentric knee joint when the polycentric knee joint is hyperextended.

In some examples of the third embodiment, the at least one powered control element can include an electric motor. The electric motor can be coupled to the thigh link and the shank link through a power screw.

The above summary is not intended to represent each embodiment or every aspect of the present disclosure. Rather, the foregoing summary merely provides an example of some of the novel aspects and features set forth herein. The above features and advantages, and other features and advantages of the present disclosure, will be readily apparent from the following detailed description of representative embodiments and modes for carrying out the present invention, when taken in connection with the accompanying drawings and the appended claims.

BRIEF DESCRIPTION OF THE DRAWINGS

The accompanying drawings exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

DETAILED DESCRIPTION

Figure 1:
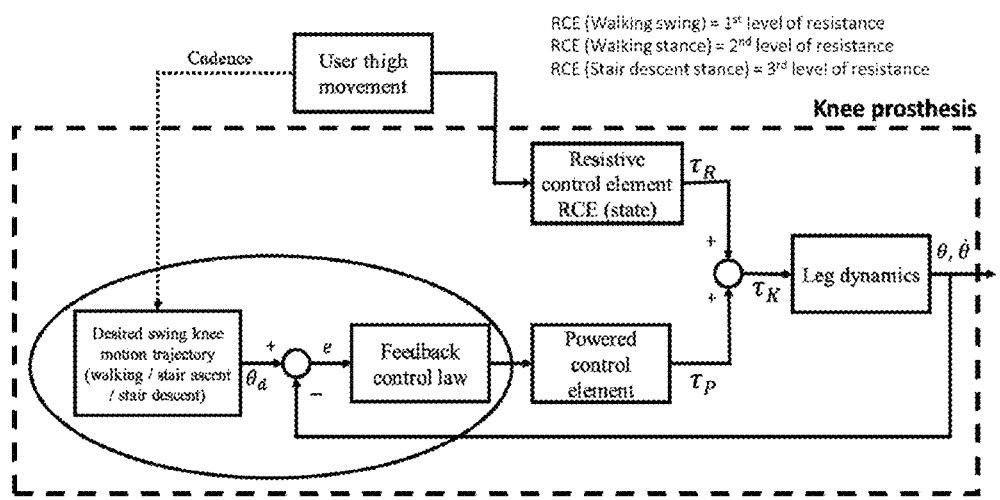
FIG. 1 shows a schematic flowchart of a swing controller, according to an exemplary embodiment.

The present invention is described with reference to the attached figures, where like reference numerals are used throughout the figures to designate similar or equivalent elements. The figures are not drawn to scale, and are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details, or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

In view of the swing-phase deficiencies associated with conventional resistive prosthetic knee devices, and the substantial weight associated with conventional powered prosthetic knee devices, various embodiments are proposed herein which provide a knee prosthesis with desirable stance and swing behaviors in a lightweight device. It is contemplated that a primarily-passive knee prosthesis with a lightweight powered actuator can provide a "swing-assist" functionality that addresses deficiencies associated with conventional prostheses, where swing-phase knee motion is provided via a strictly resistive device.

It is noted herein that the knee torque and power associated with swing phase of gait are considerably lower than the torque and power associated with stance phase. By using a passive (i.e., resistive) stance control mechanism to provide stance knee stability (i.e., stance control), and by also using passive elements in combination with the user's hip effort to produce nominally-correct swing phase motion, a swing-assist powered actuator (i.e., a powered control element) can employ a low-torque and low-power motor and drive system. Therefore, this enables a considerably lighter and smaller device than conventional prostheses, which employ powered actuators to provide control of both stance and swing.

An exemplary resistive stance control mechanism employed in stance phase can be any resistive control mechanism. In some embodiments as described below, an electrically-modulated hydraulic damper can be used. Similarly, the resistive mechanism employed in swing phase to provide nominally-correct swing-phase motion can also be conventional (e.g., fluid damping). As such, the primary role of the swing-assist actuator, according to the various embodiments discussed herein, is strictly to correct error in the nominal knee motion resulting from the passive swing-phase control device. This error can be due to variation in walking cadence, to changes in locomotion activity (e.g., walking, stair ascent, stair descent, etc.), to changes in environmental conditions (e.g., temperature, clothing, shoe weight, etc.), or to perturbations such as scuff or stumble. Because the powered actuator need only correct actions around a nominally-correct swing-phase movement, the torque and power associated with the swing-assist actuator are lower, by an order of magnitude, than those that would be required of a conventional powered knee actuator (as conventional powered knee actuators must provide for stance-phase support).

An exemplary swing-assist prosthesis can be much smaller and lighter than a fully-powered prosthesis. Because hydraulic mechanisms are known to have substantially greater torque and power density relative to electric mechanisms, the stance control aspect of the prosthesis can be much lighter than that of a fully-powered prosthesis. As the powered actuator in a swing-assist prosthesis need only produce torque and power an order of magnitude less than a fully-powered device, the powered actuator can be added with negligible added size and mass. Since the mechanical power requirements associated with swing assist are low, the electrical power requirements will also be low, and therefore the required battery can be small. As such, a stance-controlled swing-assist prosthesis can be made nearly as compact and lightweight as a stance-controlled prosthesis with a strictly passive swing behavior, and much more compact and lightweight than a fully-powered knee prosthesis that relies on powered actuation to provide the torque and power associated with stance control.

Stance Controlled Swing Assist (SCSA) Prosthesis

Figure 2:
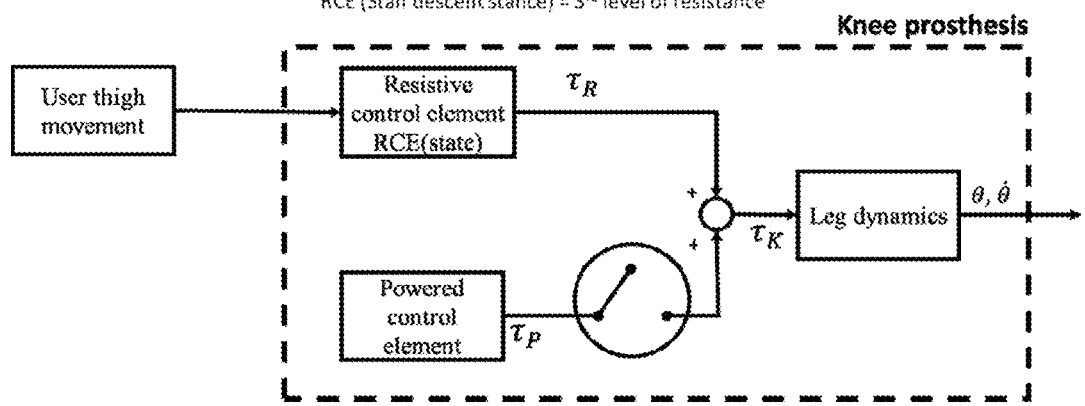
FIG. 2 shows a schematic flowchart of a stance controller, according to an exemplary embodiment.

FIGS. 1 and 2 respectively illustrate exemplary swing and stance controllers, according to embodiments contemplated herein. In both FIGS. 1 and 2, the elements inside the dashed lines can be contained within the knee prosthesis. An exemplary controller includes the elements in the circles or ovals and the setting of the RCE level of resistance (1, 2, or 3) within the RCE.

FIGS. 1 and 2 contemplate that an exemplary swing-assist knee prosthesis can provide the shown control elements, according to various embodiments. The exemplary swing-assist knee prosthesis which enables FIGS. 1-2 can include a thigh link, which is proximally connected to the user in the case of a transfemoral amputation, and a shank link, which is distally connected to an ankle or foot prosthesis. The thigh link can be rotatably connected to the shank link. The prosthesis can be further comprised of two separately-controllable elements, a resistive control element (RCE) and a powered control element (PCE), both of which impose a torque between the thigh and shank links. The RCE can be a conventional passive or resistive mechanism for providing stance knee stability and nominal swing knee resistance. An exemplary RCE for the prosthesis can be an electrically-controllable hydraulic damping element. The PCE can be a small powered actuator, capable of providing torque and power sufficient only to correct error in the nominal swing-phase motion resulting from user hip input resisted by the RCE during swing. Because the PCE is used strictly for swing-assist (i.e., error correction), the torque and power capacities of the PCE can be approximately an order of magnitude lower than the torque and power capacities of the RCE. This torque and power asymmetry between the RCE and PCE is an essential, defining aspect of a SCSA knee prosthesis.

In an exemplary embodiment, the swing-assist prosthesis employs a microprocessor-modulated hydraulic damper as the RCE. This embodiment is called a stance-controlled swing-assist (SCSA) knee prosthesis. In this type of RCE, a rotary or linear hydraulic cylinder can be connected between the thigh and shank links. Angular movement of one link relative to the other causes movement of the hydraulic fluid in the cylinder, which is typically directed through an orifice that provides resistance to fluid flow, and thus resistance to angular movement.

In one embodiment, the orifice can be an electrically-controllable valve configured with at least two settings: a large orifice setting that provides a first, relatively low level of resistance, and a small orifice setting that provides a second, relatively high level of resistance. Additional elements of the exemplary knee prosthesis are shown and discussed with respect to FIGS. 3-7, below.

As shown in FIG. 1, the first level of resistance is appropriate for providing a nominally-correct swing-phase knee movement (when swung by the user), while the second level of resistance is appropriate for providing stance knee stability during stance phase. In this embodiment, the PCE can be a small electric motor that imposes torque between the thigh and shank links via an easily backdrivable, low-torque mechanical transmission. The torque that can be sustained by the PCE is substantially smaller (e.g., an order of magnitude) than the torque that can be sustained by the RCE, particularly at the second level of resistance (i.e., when in the stance phase). The swing-assist prosthesis also includes a controller that receives signals from sensors, such as a knee angle sensor, knee angular velocity sensor, inertial measurement unit (IMU), and/or load cell that measures shank load, shank moment, or some other load. The controller employs these sensors to determine a stance state, when the prosthetic leg is in a load-bearing state, and a swing state, when the prosthetic leg is in the swing phase. This determination is sufficiently standard, and can be made using various methods for doing so, as commonly known by one skilled in the art.

In the SCSA prosthesis, the controller can operate in the stance state, according to FIG. 2. The controller can configure the RCE to use the second level of resistance to provide stance-knee stability during the stance phase (i.e., when in the stance state), and configures the RCE to use the first level of resistance to provide swing-knee resistance during the swing phase (i.e., when in the swing state). Further, the first level of resistance of the RCE is adjusted so that the nominal motion of the knee, particularly when walking at a nominal "self-selected" cadence under normal conditions (i.e., level terrain, room temperature, etc.), corresponds to a desired knee motion. This is similar to a conventional microprocessor-controlled hydraulic knee prosthesis with stance control. The SCSA prosthesis adds to this a PCE to provide swing-assist functionality. The manner in which the PCE should provide swing assist is not obvious.

In one exemplary embodiment as shown in FIGS. 1-2, a desired swing knee motion trajectory can be determined by the controller. Such desired swing knee motion trajectory can be patterned after swing knee motion during healthy gait. Just as that motion varies as a function of cadence, so can the desired swing knee motion for the SCSA. Given this desired swing knee motion, the first level of resistance of the RCE can be tuned to provide the nearest approximation of this trajectory at a nominal walking speed (e.g., at a walking speed of 1 m/s). Once this "nominal" knee behavior is established using resistive elements, a feedback control loop can be employed around the PCE, using measurement of knee angle and angular velocity to compute the error between the actual and desired knee motion.

The controller can then provide for correcting for errors in the actual knee motion relative to the set of desired swing phase knee motion trajectories. Presumably, when walking at 1 m/s under normal conditions (i.e., level terrain, room temperature, etc.), little trajectory error would exist (because the RCE was tuned to provide appropriate motion under these conditions). Therefore, the PCE presumably does not contribute torque to the motion. As the conditions vary, however, the RCE cannot adequately adapt; however, the PCE, which is highly adaptable, will make corrections as necessary.

For example, if walking in cold temperatures, the oil in a hydraulic cylinder changes properties substantially, and the nominal motion provided by the RCE in swing phase will not provide appropriate motion. In this case, the feedback loop around the PCE can add energy as needed to the motion to provide the desired swing phase knee motion. This does not require measurement of temperature, or knowledge of how the resistive properties of the oil change with temperature, which would be non-trivial to include in an RCE controller. Similarly, in the case of scuffing (or stumbling), energy is removed from the swinging leg. In a conventional leg, no mechanism exists to add power to the knee to recover the original swing phase trajectory. In the case of the SCSA prosthesis according to these embodiments, the PCE can immediately inject power into the knee to attempt to recover the original swing phase trajectory, and thereby prevent a fall.

Alternate embodiments can also contemplate swing motion when walking up or down stairs, which require a very different swing phase motion than normal walking. In order to provide improved functionality during stair ascent and descent, the SCSA prosthesis of these embodiments can include stair functionality. In such a case, the controller can additionally identify stair descent and stair ascent states, including swing and stance states for each. As shown in FIGS. 1-2, the RCE can employ at least three levels of resistance: a first level corresponding to a nominal level of resistance appropriate for swing phase during walking; a second level of resistance that can provide stance-knee stability during walking; and a third level of resistance that can provide stance-knee yielding appropriate for stair descent.

When walking upstairs, a user can walk with a step-to gait, relying on his or her sound leg to ascend, rather than walking with a step-over gait. In a step-to gait, the stance behavior of the knee prosthesis during stair ascent is similar to the stance-phase behavior in walking (i.e., provide knee stability against buckling). In this embodiment, the controller configures the RCE to use the first level of resistance to provide a nominal swing-phase behavior (i.e., desired trajectory for walking at a given self-selected cadence); configures the RCE to use the second level of resistance to provide knee stability during walking and stair ascent; and configures the RCE to use the third level of resistance to use the third level of resistance to provide knee yielding during the stance phase of stair descent.

In the case of an embodiment with stair functionality, the controller further includes a desired swing-phase knee motion corresponding to the stair ascent state, and another corresponding to the stair descent state. During the swing phase of each activity (i.e., walking, stair ascent, stair descent), the RCE set to the first level of resistance can provide a nominal swing-phase knee motion (as in a conventional prosthesis), while the PCE can provide corrective action relative to the nominal knee motion. Therefore, these embodiments provide a swing-phase motion that is robust to perturbation, and appropriate for each activity.

For example, during stair ascent, conventional prosthesis thigh and shank motion is typically too slow to provide sufficient inertial coupling, and therefore the knee flexes very little. A user will typically circumduct his or her hip to swing the essentially straight knee onto the next successive stair. The PCE can provide the knee flexion and subsequent extension to enable a user to ascend stairs in a step-to manner without employing hip circumduction. Stair descent with a conventional prosthesis, although it can be conducted in a step-over manner, similarly suffers from the fact that the nominal swing-phase knee motion, when provided solely by the resistive RCE, is compromised relative to what would best benefit the user, with regard to placing his or her foot on the next successive stair in preparation for stair descent stance phase. The PCE and the various embodiments herein rectify this problem and facilitate safer stair descent.

Figure 3:
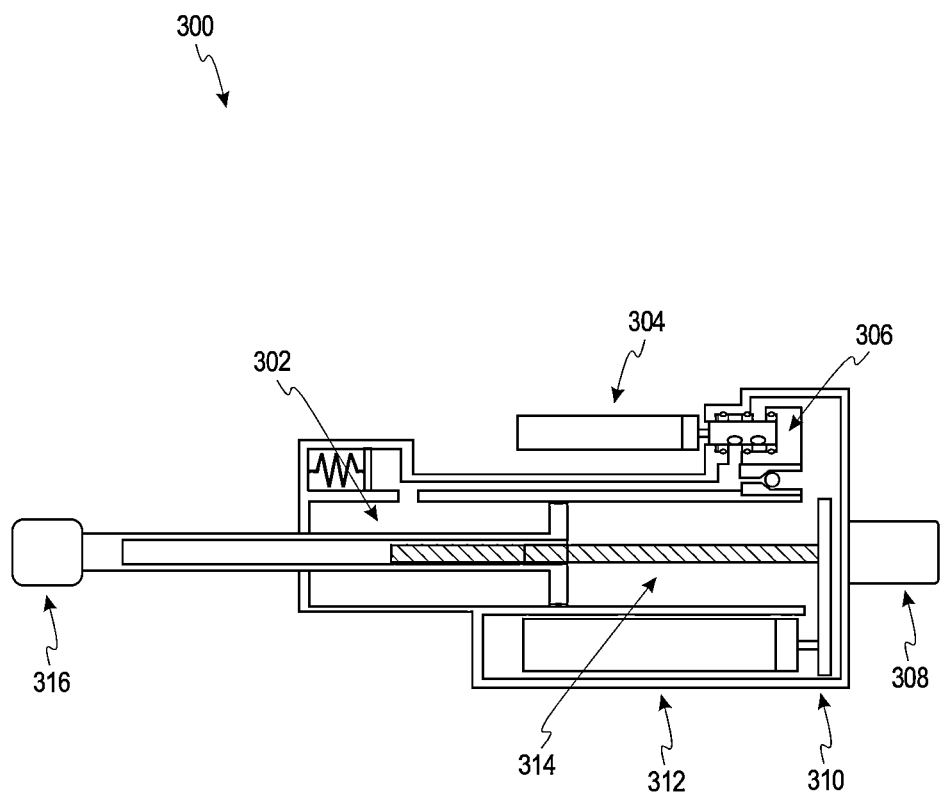
FIG. 3 shows a schematic drawing jointly packaged resistive control element (RCE) and powered control element (PCE), according to an exemplary embodiment.

FIG. 3 shows a schematic rendering of one embodiment 300 of an RCE packaged within the same structure as a separate PCE. This embodiment 300 can include an RCE hydraulic cylinder 302, a motor 304, an RCE hydraulic valve 306, a shank link connection 308, a PCE gear train 310, a PCE electric motor 312, a PCE power screw transmission 314, and a thigh link connection 316.

Figure 4:
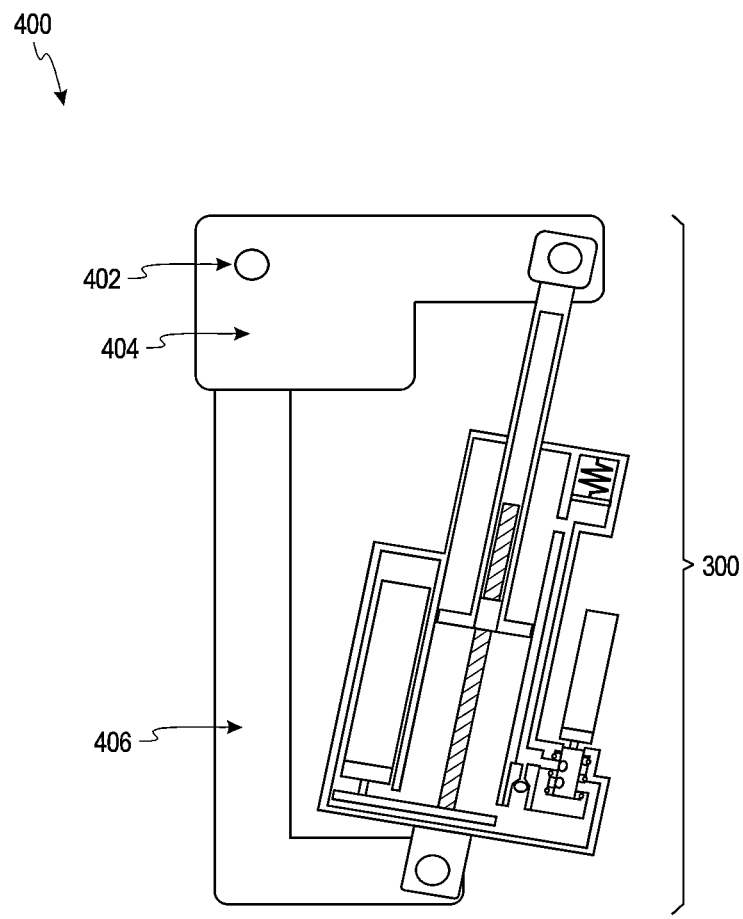
FIG. 4 shows a schematic drawing of an RCE/PCE actuation unit which resists or powers knee rotation, according to an exemplary embodiment.

In this embodiment, the RCE is comprised of a hydraulic cylinder 302, mechanically coupled to a knee joint (shown further in FIG. 4). Resistance to knee joint rotation results from hydraulic fluid flow through a hydraulic valve 306, where the hydraulic fluid flow is generated by relative motion between a thigh link and shank link (i.e., by knee joint rotation). FIG. 3 shows that the hydraulic valve 306 can be configured by a valve motor 304, which can position the valve 306 in varying orientations to modulate the resistance to fluid flow, and thus to knee rotation. Furthermore, despite the fact that the RCE is controlled by a motor 304, the RCE fundamentally cannot provide power to the knee joint, but rather can only resist knee joint motion. The valve motor 304, rather, can only vary the extent to which the RCE resists knee motion. In some preferred embodiments, the valve 306 can be configured to provide a first and second level of resistance to knee motion. In other preferred embodiments, the valve 306 can be configured to provide a first, second, and third level of resistance to knee motion (as discussed previously with respect to FIGS. 1-2).

FIG. 3 also shows a preferred embodiment of a PCE, which is separate from the RCE, but packaged together with it. In order to increase compactness and decrease weight of the system 300, PCE connects to the thigh link and shank link via the same connecting rod. FIG. 3 shows that the PCE can include an electric motor 312, which transmits power to the knee joint through a power screw 314 located inside the piston rod of the hydraulic cylinder 302. As shown in FIG.

3, the electric motor 312 may also connect to the power screw 314 through a set of gears 310.

FIG. 4 shows another exemplary system 400 of the combination actuation unit of an RCE and a PCE, according to one embodiment. System 400 includes system 300, and further includes a knee joint 402, a thigh link 404, and a shank link 406.

Figure 5A:
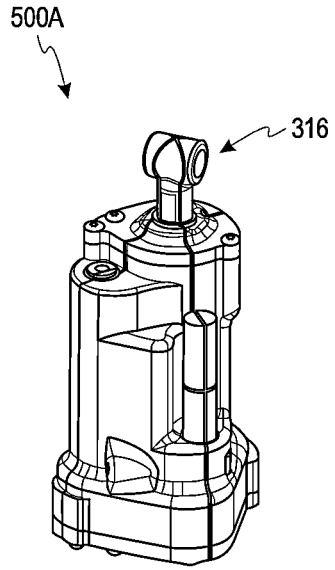
FIG. 5A shows an exemplary exterior view of an RCE/PCE actuation unit, according to one embodiment.
Figure 5B:
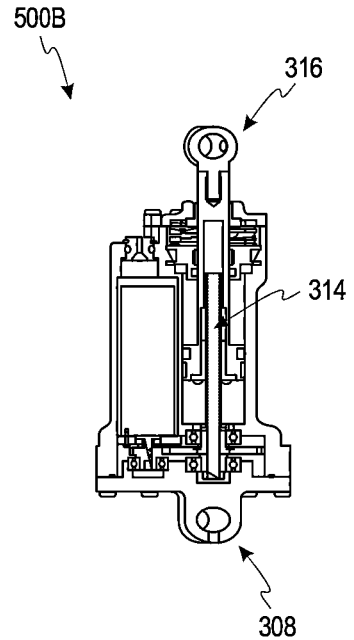
FIGS. 5B-5C show exemplary cut-away views an RCE/PCE actuation unit, according to one embodiment.
Figure 5C:
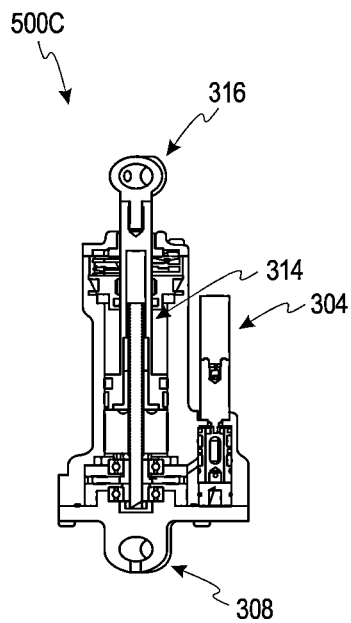

Another design embodiment of the RCE/PCE actuation package is shown in FIGS. 5A-5C. FIG. 5A shows an external perspective 500A of an exemplary actuation package; FIG. 5B provides a cross-section view 500B through the PCE axis of the actuation package; FIG. 5C provides a cross-section view 500C through the RCE axis of the actuation package. FIGS. 5A-5C include similar elements and corresponding numbers to the elements and numbering of FIG. 3.

Figure 6:
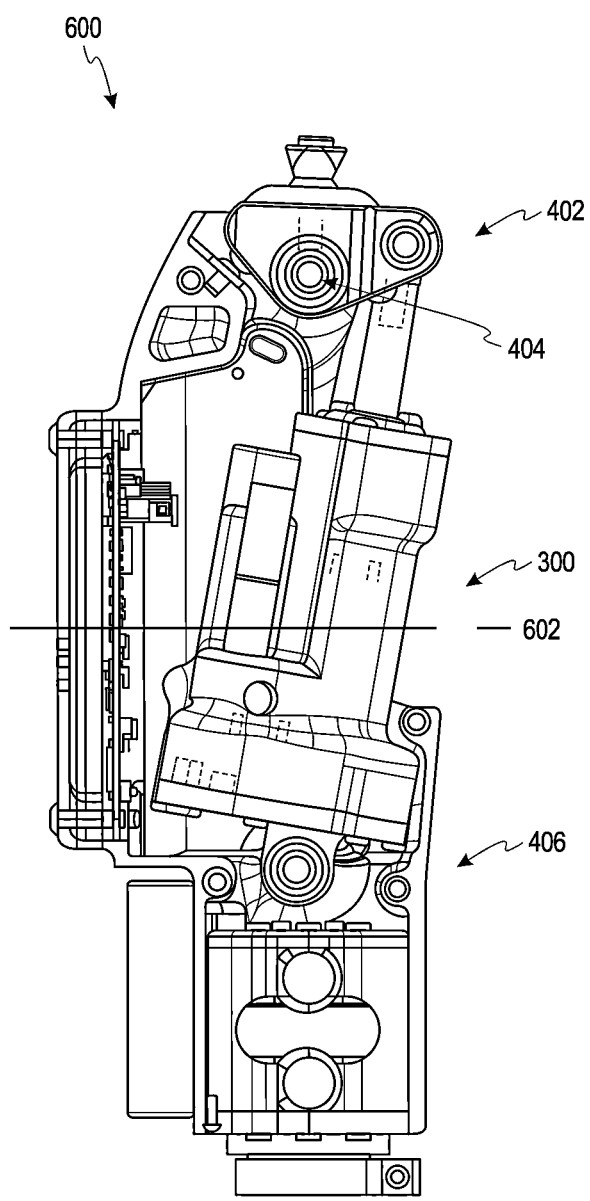
FIG. 6 shows an exemplary stance controlled swing assist (SCSA) prosthesis in a fully-extended configuration, according to one embodiment.
Figure 7:
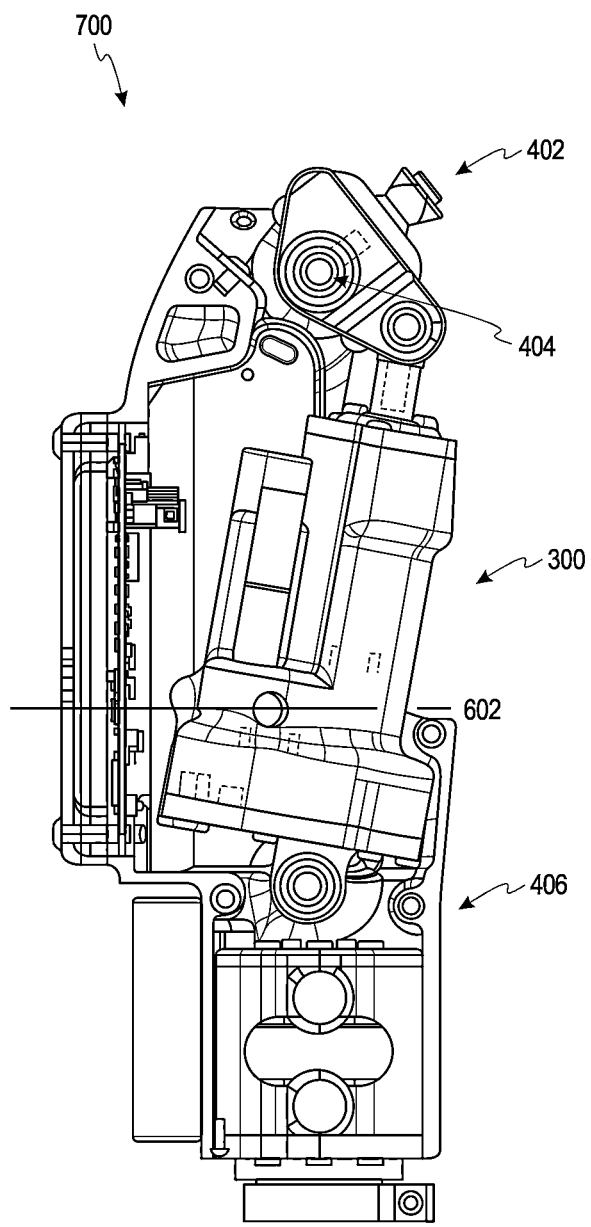
FIG. 7 shows an exemplary SCSA prosthesis in a fully-extended configuration, according to one embodiment.

FIGS. 6-7 show design embodiments of the SCSA knee using the RCE/PCE actuation package, with the left cover removed. FIG. 6 shows the knee in a fully-extended position 600 and FIG. 7 shows the knee in a partially-flexed configuration 700. FIGS. 6-7 include similar elements and corresponding numbers to the elements and numbering of FIGS. 3 and 4. In addition, FIGS. 6-7 show a horizontal axis 602. Altogether FIGS. 6-7 demonstrate an exemplary amount of movement for an exemplary prosthesis, according to the various embodiments.

Experimental Data: SCSA Prosthesis

FIGS. 8A-10F show experimental results of swing-assist benefits. In these experiments, the subject first conducted walking trials at each of three speeds with a conventional stance-controlled passive knee prosthesis (shown in FIGS. 8A, 8C, and 8E). The three speeds were based on his self-selected speed (0.9 m/s) (shown in FIGS. 8C and 8D), and 20% slower (shown in FIGS. 8A and 8B) and faster (shown in FIGS. 8E and 8F) respectively (0.7 m/s and 1.1 m/s). The subject walked at a steady-state speed for 45 sec of data collection for each speed.

Figure 8A:
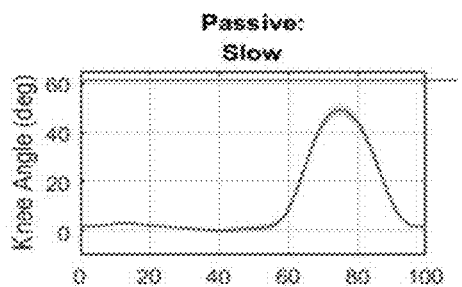
FIGS. 8A-8F show experimental data of knee angles across different speeds, as compared between a conventional passive prosthesis and an exemplary SCSA prosthesis, according to one embodiment.
Figure 8B:
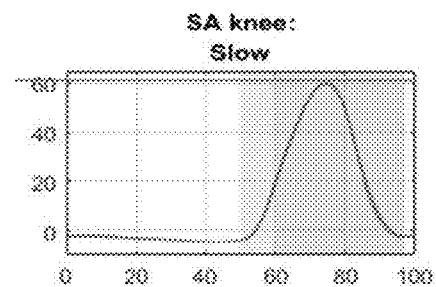
Figure 8C:
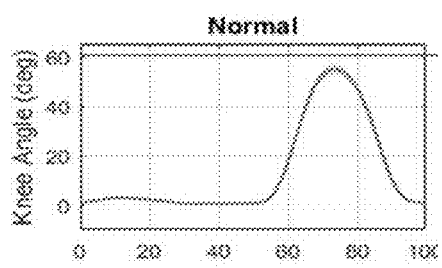
Figure 8D:
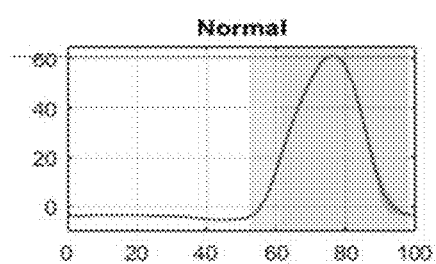
Figure 8E:
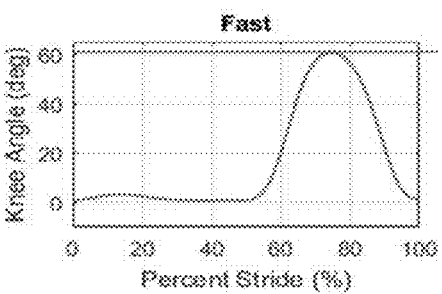
Figure 8F:
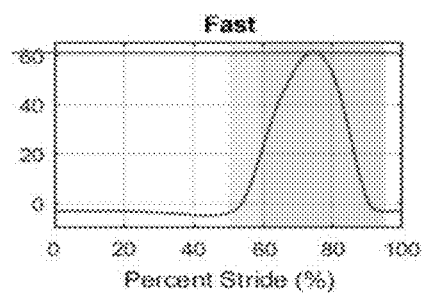

Following data collection with the passive prosthesis, the subject was fit with the SCSA prosthesis and repeated the treadmill experiments at the same three treadmill speeds and with the same experimental protocol employed with the passive prosthesis (shown in FIGS. 8B, 8D, and 8F).

FIGS. 8A-8F demonstrate the knee angle versus stride for each walking speed with the daily-use prosthesis, compared to those for the SCSA knee prosthesis. Each plot shows the mean of 25 strides, and also plus and minus one standard deviation about the mean. The data were parsed using heel strike, which was detected by ground reaction force measurement. The passive prosthesis (shown in FIGS. 8A, 8C, and 8E) resulted in peak knee flexion angles of 49.2, 55.0, and 60.7 deg at the three walking speeds, respectively, while the SCSA prosthesis (shown in FIGS. 8B, 8D, and 8F) resulted in peak knee flexion angles of 59.9, 61.1, and 61.4 degrees, respectively. In relative terms, the peak flexion angle of the passive prosthesis (shown in FIGS. 8A, 8C, and 8E) varies by plus/minus 10% when walking speed varies by plus/minus 20%, while the SCSA prosthesis (shown in FIGS. 8B, 8D, and 8F) peak knee flexion angle varies by only plus/minus 1% for the same speed variation.

Figure 9A:
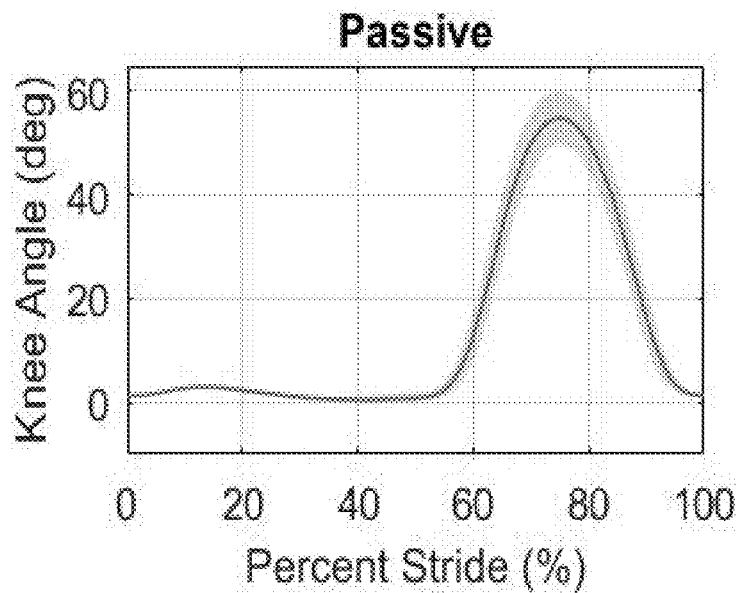
FIGS. 9A-9B show experimental data of knee angles across all speeds, as compared between a conventional passive prosthesis and an exemplary SCSA prosthesis, according to one embodiment.
Figure 9B:
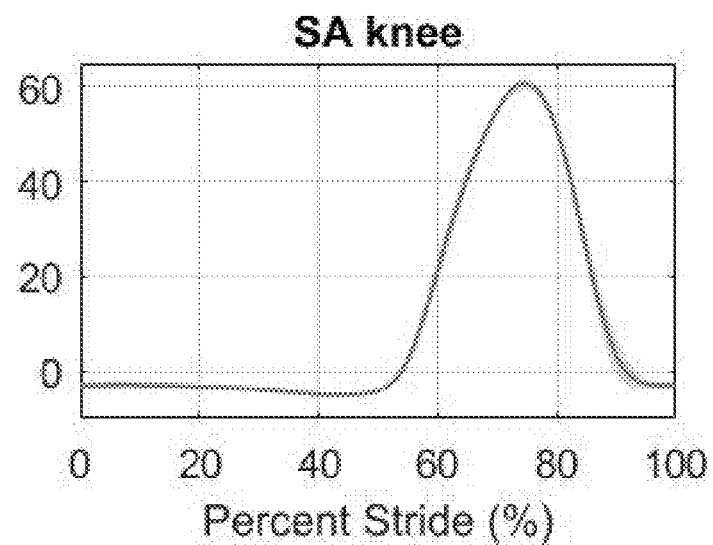
Figure 10A:
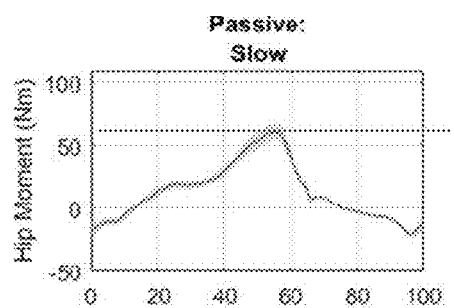
FIGS. 10A-10F show experimental data of side-hip moments, as compared between a conventional passive prosthesis and an exemplary SCSA prosthesis, according to one embodiment.
Figure 10B:
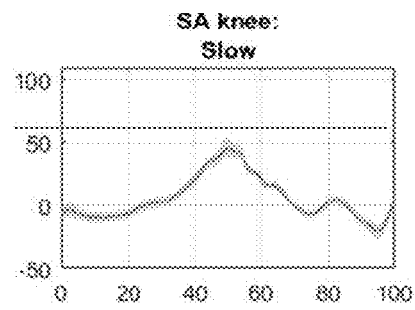
Figure 10C:
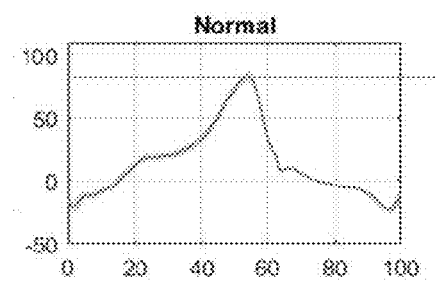
Figure 10D:
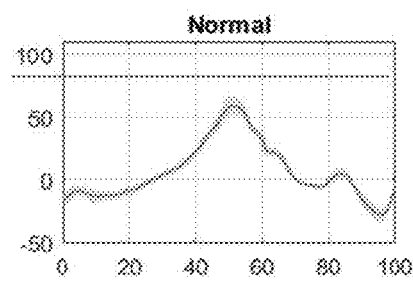
Figure 10E:
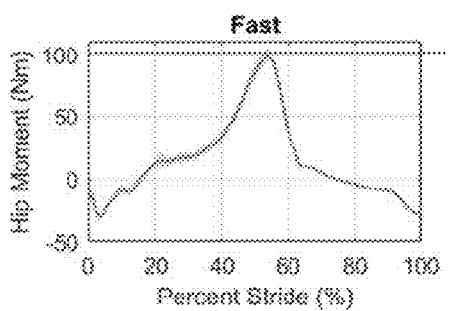
Figure 10F:
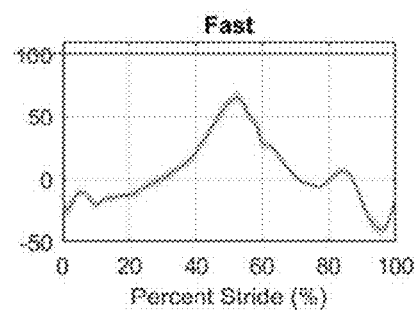
Figure 11A:
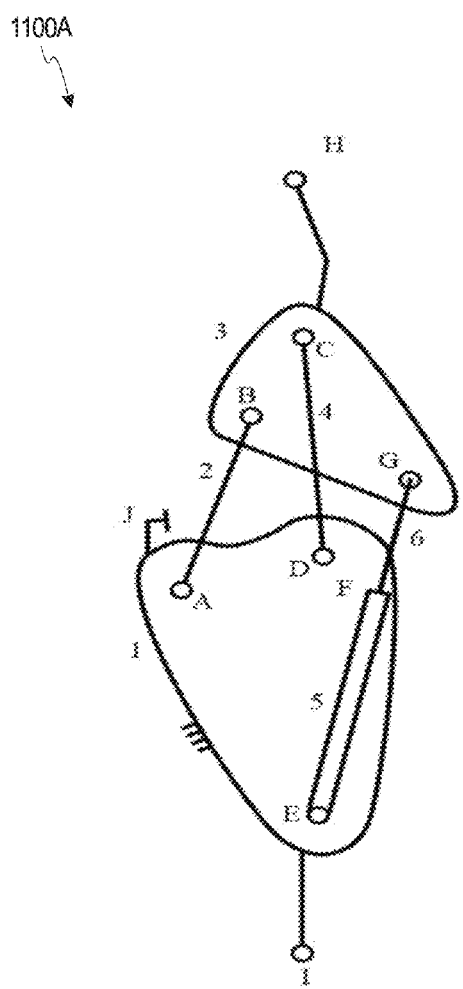
FIGS. 11A-11B show a schematic drawing of an exemplary 6-bar PSA prosthesis, according to one embodiment.
Figure 11B:
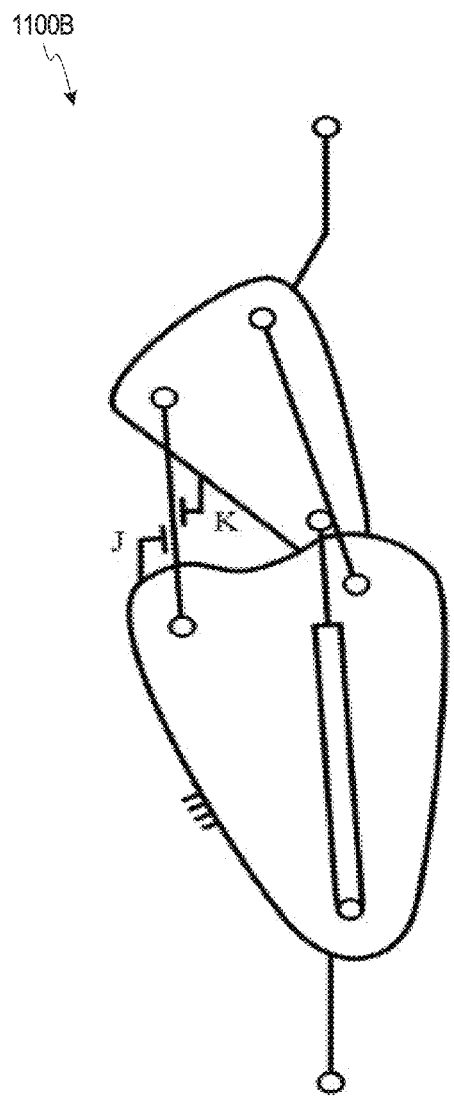

FIGS. 9A-9B show the knee angle data collected across all three walking speeds; the difference in standard deviation provides another indication of the improved swing-phase uniformity offered by the SCSA prosthesis (FIG. 9B), relative to the passive conventional prosthesis (FIG. 9A)

FIGS. 10A-10F show the affected-side hip moment for each prosthesis at each speed, averaged across the 25 strides at each speed. As seen in FIGS. 10A-10F, the SCSA prosthesis (shown in FIGS. 10B, 10D, and 10F) required significantly lower peak hip torques at the initiation of swing relative to the daily-use prosthesis (shown in FIGS. 10A, 10C, and 10E). For slow (shown in FIGS. 10A-10B), normal (shown in FIGS. 10C-10D), and fast walking (shown in FIGS. 10E-10F), the SCSA knee (shown in FIGS. 10B, 10D, and 10F) required 23.7%, 27.1%, and 33.3% less peak hip torque, respectively, at swing initiation.

Based on the data as shown in FIGS. 8A-10F, the addition of swing assist in the SCSA knee provides a more repeatable and consistent swing-phase motion across walking speeds compared to a conventional passive prosthesis, while maintaining a similar size, weight, and low-noise operation. Further, FIGS. 10A-10F indicate that the SCSA prosthesis provides a substantial reduction in peak hip torque required to initiate swing. These results indicate the ability of the SCSA knee prosthesis to provide greater consistency and lower effort to user during swing phase, with little added size and weight of the associated swing-assist mechanism.

Polycentric Swing-Assist Knee Prosthesis

Rather than provide stance knee stability via a modulated hydraulic dissipater, as in the case of an SCSA knee prosthesis, it is contemplated that stance knee stability can alternatively be provided using a polycentric knee mechanism. This embodiment can be referred to as a polycentric swing-assist (PSA) knee prosthesis. An exemplary embodiment of the PSA prosthesis is a 4-bar polycentric knee, configured with a linear motor drive system for swing assist, which together comprise a single degree-of-freedom (DOF) 6-bar mechanism, as shown in FIGS. 11A-14D (discussed below). In the combined mechanism, the 4-bar provides stance-knee stability (i.e., passive stance control) by locating the instant center of rotation (ICR) posterior to the ground reaction force (GRF) when the knee is fully extended. A small motor powers the slider axis (i.e., the extension and retraction of the sliding links) in the slider-crank mechanism. The combined 6-bar is designed to maintain the ICR of the 4-bar posterior to the slider axis throughout the range of motion (ROM), which enables the motor to provide power-assisted swing. The result is a lightweight device that provides robust stance and swing behaviors. A detailed description of this mechanism follows, along with a method for providing active swing assist to complement the passive stance control.

Therefore, an exemplary PSA prosthesis includes the following essential characteristics: 1) employs a 4-bar geometry to provide passive stance-knee stability during stance phase; 2) provides an axis of knee rotation substantially coincident with the anatomical axis of knee rotation during swing phase; 3) employs a motor to provide power-assisted swing motion; and 4) is configured to fit within a compact design envelope appropriate for a knee prosthesis. These features are achieved by employing the specific 6-bar configuration shown schematically in FIGS. 11A-11B. The 6-bar linkage is comprised of shank link 1; thigh link 3; revolute connecting links 2 and 4; and prismatic connecting links 5 and 6. The mechanism is further comprised of revolute joints A, B, C, D, E, and G, and prismatic joint F. The mechanism is additionally comprised of thigh attachment point H; shank attachment point I; and extension stops J and K. Note that FIG. 11A omits extension stop K for clarity; extension stop K is instead included in FIG. 12B.

Figure 12:
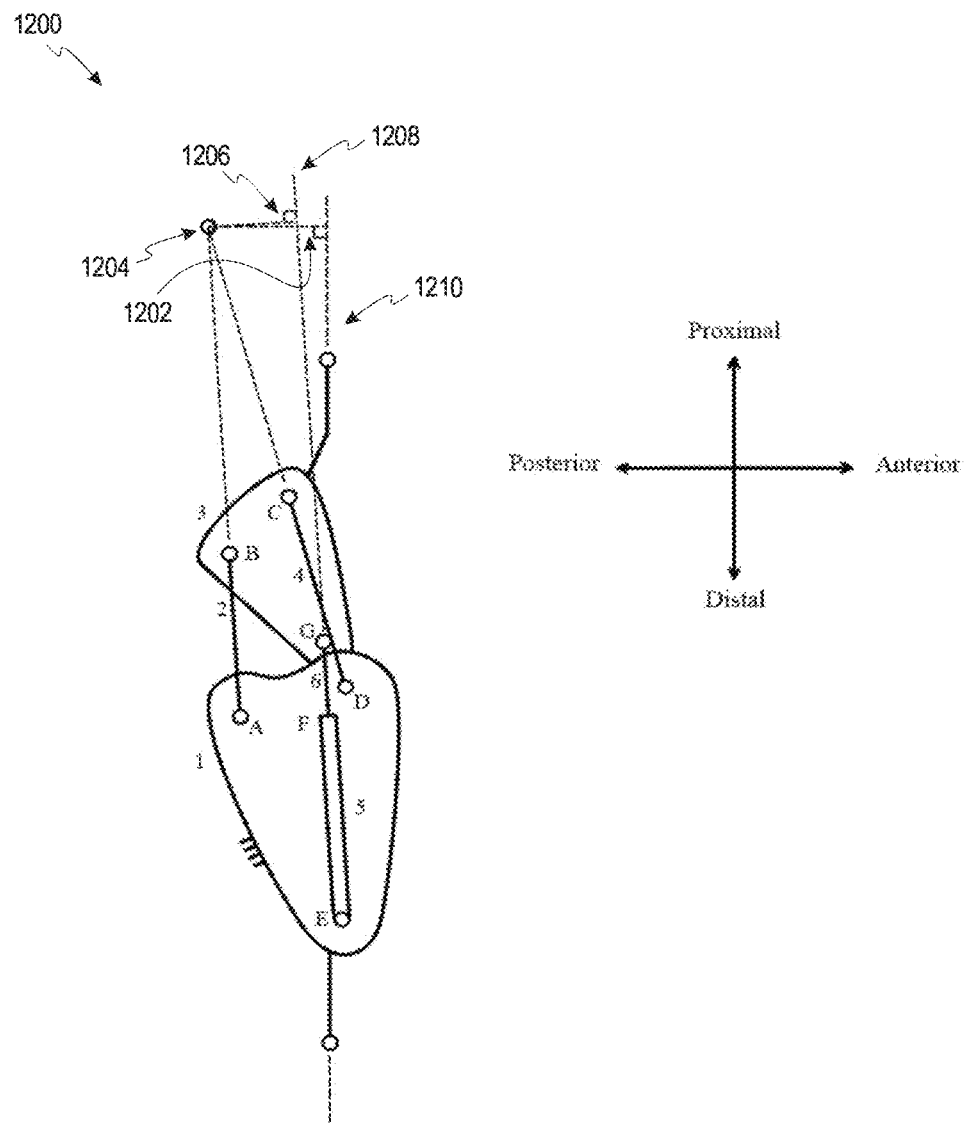
FIG. 12 shows a schematic drawing of the geometric conditions that must be satisfied by an exemplary prosthesis, according to the various embodiments.

In order to provide the aforementioned characteristics, the 6-bar linkage must satisfy several geometric conditions in various positional configurations. FIG. 12 shows a system 1200 where the various geometric considerations must be met. System 1200 includes similar elements and numbering as systems 1100A and 1100B of FIGS. 11A and 11B. In addition, system 1200 includes, a stance arm lever 1202, an ICR31 1204, an actuator lever arm 1206, an actuator force line 1208, and a trochanter-knee-ankle (TKA) line 1210. The instantaneous center of rotation (ICR) 1204 of link 3 relative to link 1, given by ICR31 1204, is defined as the intersection of lines collinear with links 2 and 4 and extending from them. The TKA line 1210 is defined as the line collinear with points H and I and extending through them when the knee is in the fully-extended state. In such a state, the TKA line 1210 extends nominally along the long axis of the thigh and shank. Note that the TKA line 1210 is not clearly defined when the knee is in a flexed state. The stance lever arm 1202 is defined as the normal distance from the TKA line 1210 to the ICR31 1204 (in the fully-extended state). The actuator force line 1208 is defined as the line collinear with joints E, F, and G. The actuator lever arm 1206 is defined as the normal distance from the actuator force line 1208 to the ICR31 1204.

Given these definitions, the geometric conditions the mechanism must satisfy are as follows. In the fully-extended configuration, link 2 is prevented from counterclockwise rotation relative to link 1, either by extension stop J or extension stop K. Additionally, in the fully-extended configuration, ICR31 1204 should lie posterior to the TKA line 1210 to provide stance-knee stability during the stance phase of gait. Given this configuration, a load that is nominally directed along the TKA line 1210 will establish an extension torque on link 3, equal to the force along the TKA line times the stance lever arm 1202, which will act to rotate link 2 counterclockwise, which will maintain link 2 against extension stop J or K, thus promoting stance knee stability. The linkage defined by ABCD must be such that, in all configurations other than the fully extended, link 2 is rotated away from extension stops J and K.

Once slightly flexed from the fully-extended configuration, the behavior of the knee prosthesis can switch functions from stance to swing functionality. In stance phase, when the knee is in the fully-extended configuration, the ICR31 1204 is posterior to the anatomical knee center. In that configuration, the knee is effectively locked in that configuration. Because the knee prosthesis does not flex, the location of the ICR31 1204 away from the anatomical knee is not problematic. When the knee flexes in swing phase, however, it is important that the prosthesis provide a motion representative of healthy lower limb motion, which requires that the nominal knee center of rotation be near the anatomical knee joint. This is achieved by configuring the geometry of the 4-bar associated with joints A, B, C, and D such that lines collinear with links 2 and 4, respectively, intersect within links 2 and 4. This can be referred to as a cross-link configuration. In this cross-link configuration, the ICR31 1204 will lie at the intersection of links 2 and 4, and thus by design will be located near the anatomical knee joint. Thus, the 4-bar ABCD should be configured such that links 2 and 4 remain in a cross-linked configuration from the slightly-flexed configuration to the fully-flexed configuration, in which case the shank link will rotate relative to the thigh link about an axis near the anatomical knee joint throughout the range of knee flexion.

In order to provide an effective power assist during the swing phase, the actuator should be capable of applying a torque on the thigh link relative to the shank link throughout the full range of motion (ROM) of the knee. In order to do so, the actuator force line 1208 must not cross the ICR31 1204 throughout the full ROM of the knee (i.e., the actuator force line must remain either anterior to the ICR31 1204, or posterior to it, throughout the ROM). As previously stated, the ICR31 1204 must be located posterior to the TKA line 1210 to promote stance knee stability. Further, in order to provide a maximally compact arrangement of components, the actuator force line should be substantially aligned with the TKA line 1210 (i.e., the linear actuator associated with extending link 6 relative to link 5 should be aligned with the anatomical shank). Since the TKA line 1210 is necessarily anterior to the ICR31 1204 in the fully-extended state; since the actuator force line is substantially aligned with the TKA line 1210; and since the actuator force line 1208 cannot cross the ICR31 1204 throughout the ROM, the linkage should be configured such that the ICR31 1204 remains posterior to the TKA line 1210 throughout the ROM. As a result, in all configurations of the 6-bar, the mechanism is configured such that the actuator force line (i.e., line collinear with EFG) remains anterior to the ICR31 1204 (i.e., intersection of lines collinear respectively with links 2 and 4). Further, in many embodiments, the powered swing assist will benefit from an even distribution of active torque throughout the range of motion, and as such, the 6-bar linkage should be configured such that the actuator lever arm remains largely invariant throughout the knee ROM.

In some cases of conventional 4-bar prosthetic knees, the 4-bar mechanisms are designed to bring the ICR31 1204 anterior to the TKA line 1210 as the knee begins to flex, in an effort to generate a flexion torque and promote the initiation of swing. Such a configuration would not, however, enable the actuator force line 1208 to be substantially aligned with the TKA line 1210, since the ICR31 1204 in this case would necessarily cross the TKA 1210 and actuator force lines 1208. In such a case, an actuator force line 1208 can be configured to always remain posterior to the ICR31 1204, but doing so would not allow the linear actuator to be substantially aligned with the anatomical shank, and thus would result in an undesirable arrangement.

Figure 13A:
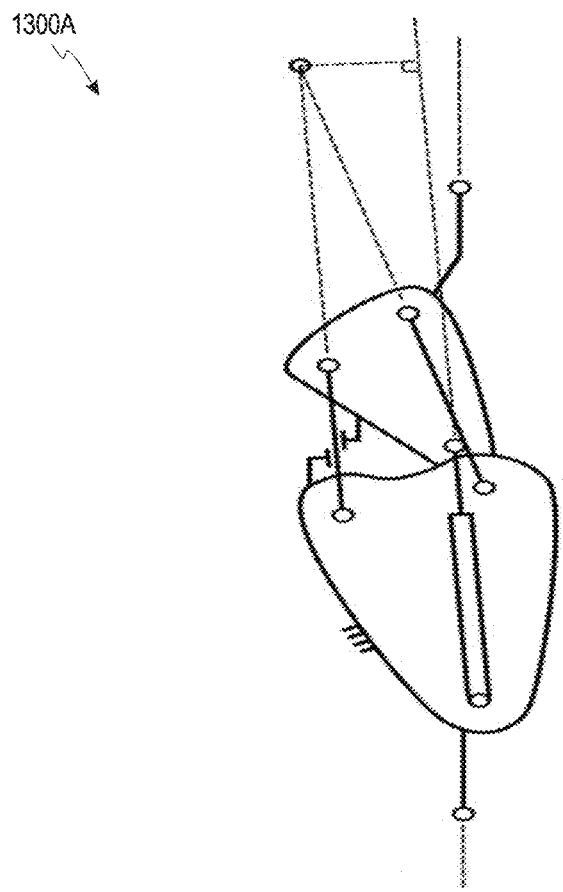
FIGS. 13A-13D show exemplary schematic drawings of a 6-bar mechanism satisfying the geometric conditions of FIG. 12, according to one embodiment.
Figure 13B:
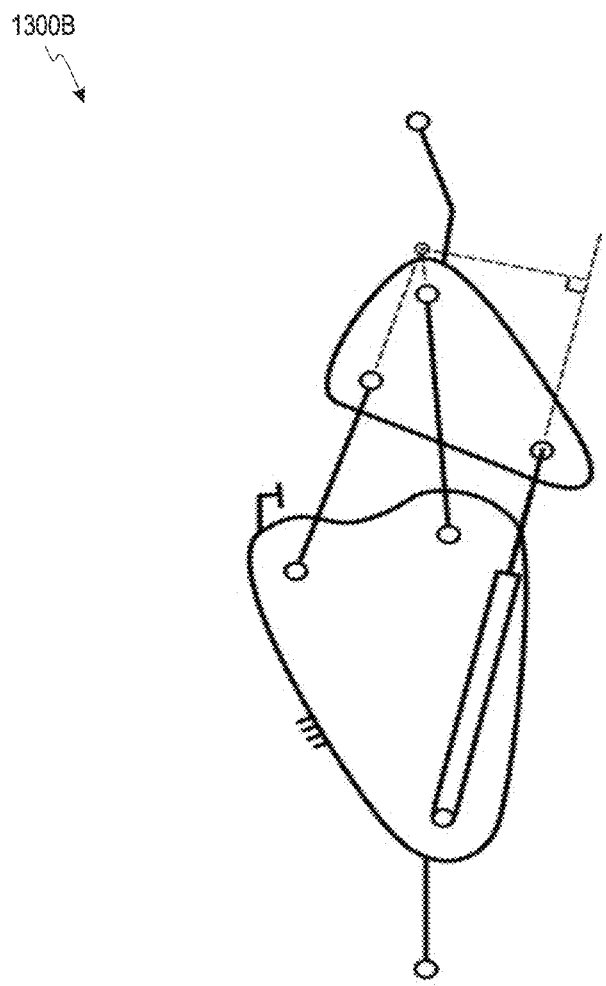
Figure 13C:
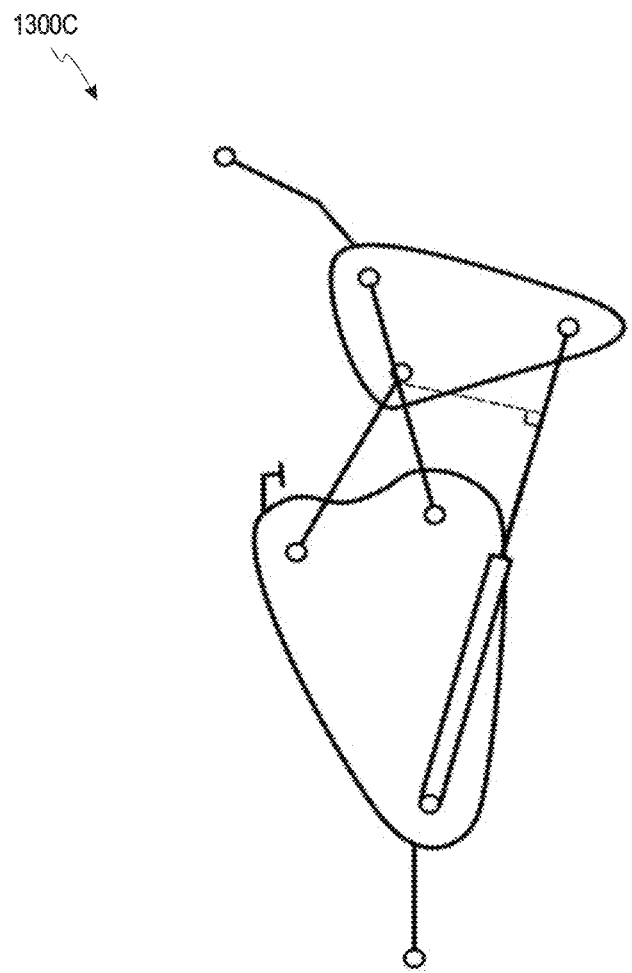
Figure 13D:
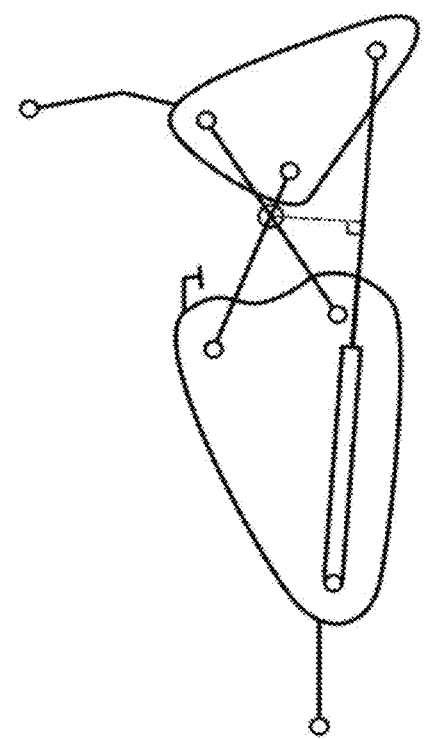
Figure 14A:
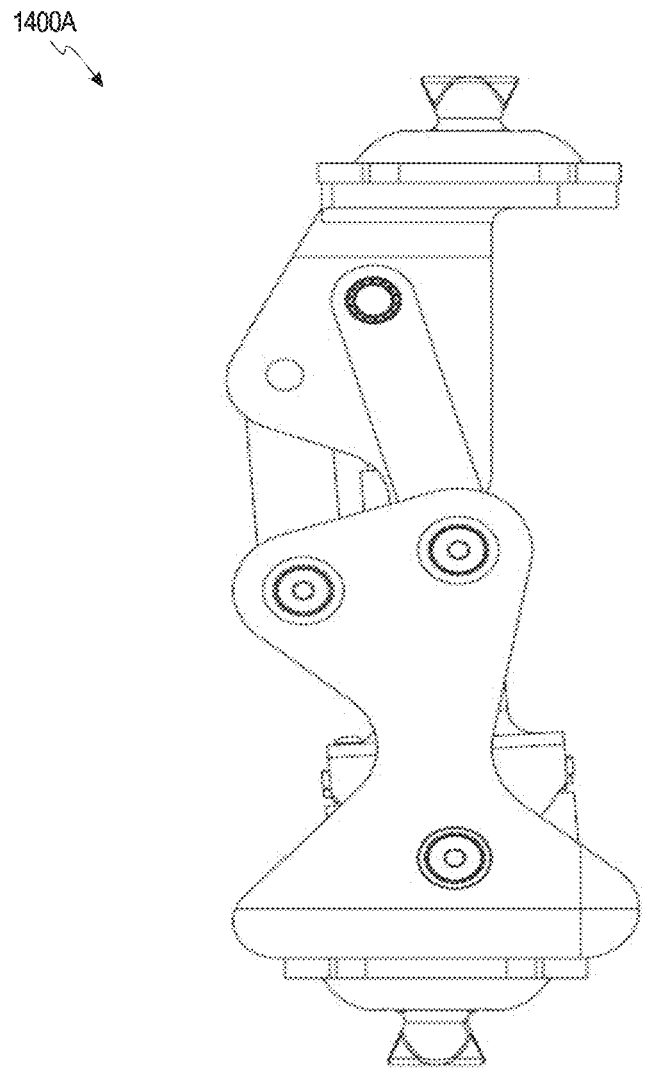
FIGS. 14A-14D show additional schematic drawings of a 6-bar mechanism satisfying the geometric conditions of FIG. 12, according to one embodiment.
Figure 14B:
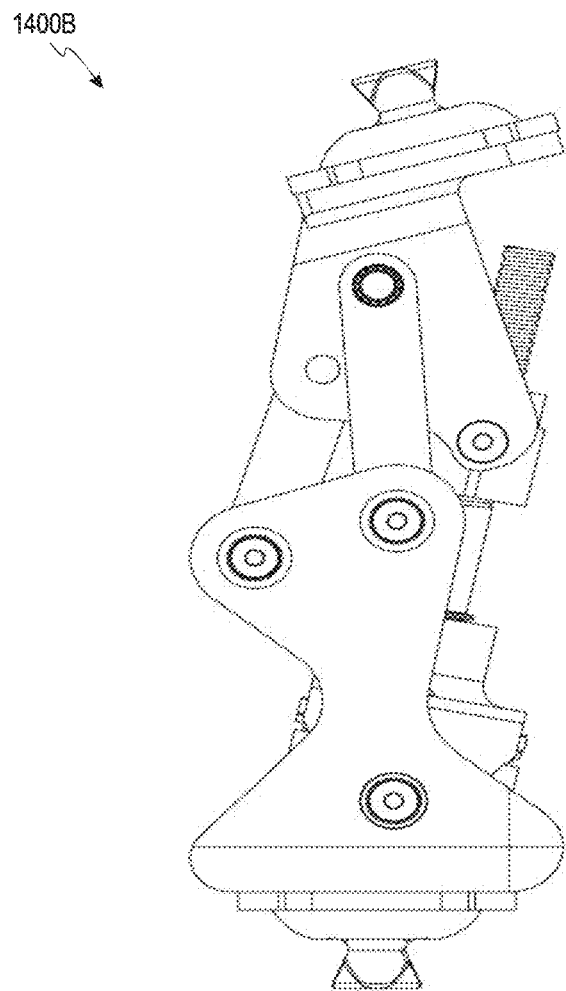
Figure 14C:
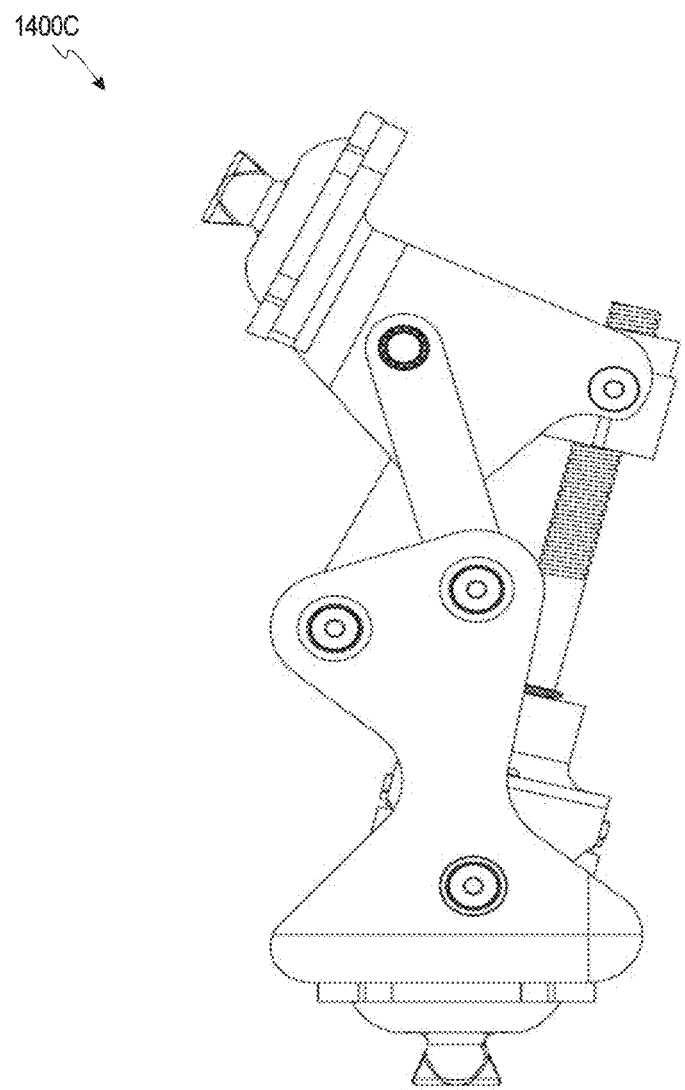
Figure 14D:
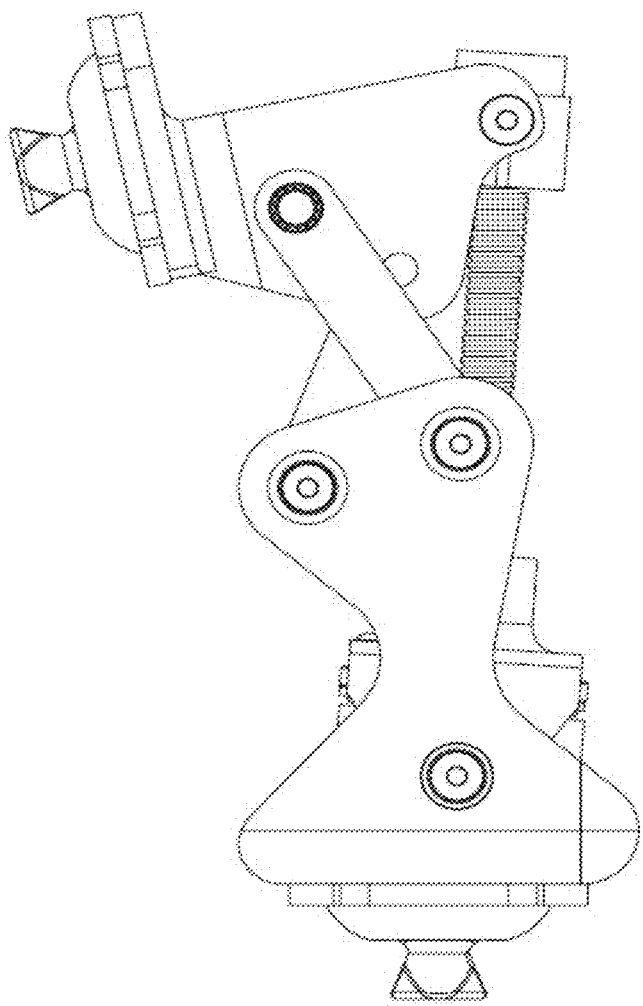

The aforementioned characteristics are illustrated in the 6-bar mechanism shown in FIGS. 13A-13D. FIGS. 13A-13D include similar elements and numbering as systems 1100A and 1100B of FIGS. 11A and 11B. Specifically, FIGS. 13A-13D show the 6-bar linkage in four representative configurations, which are fully-extended (FIG. 13A); slightly-flexed (FIG. 13B); substantially-flexed (FIG. 13C); and fully-flexed (FIG. 13D). With respect to the previously described linkage characteristics in the fully-extended state, it can be seen in FIG. 13A that the ICR31 1204 is located posterior to the TKA line 1210; the actuator force line is substantially aligned with the TKA line 1210; and the extension stops prevent clockwise rotation of link 2. Following slight flexion, as shown in FIG. 13B, the ICR31 1204 moves from the location posterior to the TKA line 1210 in the fully-extended state to a location nominally at joint C; link 2 moves away from extension stops J and K; and actuator lever arm 1206 remains similar to that in the fully-extended state. As the knee flexes further, as illustrated in FIGS. 13C and 13D, the ICR31 1204 travels from joint C along link 4 toward joint D, and thus remains near to the anatomical knee. Further, in the configurations shown in FIGS. 13C and 13D, the actuator lever arm 1206 remains essentially the same as in the other configurations. Finally, the actuator force line 1208 (i.e., collinear with EFG) remains substantially aligned with the shank axis, which facilitates compact packaging for the knee prosthesis. Note also that the ICR31 1204 remains posterior to the actuator force line 1208 in all configurations, and that link 2 remains rotated away from extension stops J and K in all flexed configurations.

FIG. 14 shows a physical embodiment of the 6-bar mechanism. Specifically, FIGS. 14A-14D show a physical embodiment of the 4-bar knee with power-assist swing illustrated in FIGS. 14A-14D, where FIG. 14A shows the knee in a fully-extended configuration; FIG. 14B shows the knee in a slightly-flexed configuration; FIG. 14C shows the knee in a substantially-flexed configuration; and FIG. 14D shows the knee in a fully-flexed configuration. FIG. 12 includes similar elements and as systems 1100A and 1100B of FIGS. 11A and 11B. In the design embodiment, the prismatic connecting links 5 and 6 and prismatic joint F are embodied by a motorized drive assembly. The motorized drive assembly is comprised of a power screw assembly (prismatic connecting link 5) and a nut assembly (prismatic connecting link 6). The power screw assembly is comprised of a motor housing, a motor shaft, and a power screw rotatably affixed to the motor shaft. The nut assembly is comprised of at least a power screw nut and a nut housing. The motor housing is pivotably connected to the shank link at joint E, and the nut housing is pivotably connected to the thigh link at joint G. The power screw translates relative to the power screw nut as the motor drives the power screw, thus establishing powered prismatic motion at joint F.

PSA Swing Control

The PSA swing-assist control can employ the controller used in the SCSA swing-assist control. Since a PSA knee may not employ a dedicated RCE, however, the controller can be configured with some differences. Like in the SCSA prosthesis, the PCE can be easily backdrivable, and the user initiates swing in the same manner he or she initiates swing in a conventional prosthesis with passive stance and swing control mechanisms. In this embodiment, the swing control is not active in the initiation of swing; rather, once swing has been initiated to an extent that the swing foot is substantially unloaded, the active swing controller imposes swing control on the remainder of the swing-phase motion.

In an exemplary embodiment, the prosthesis controller takes the form of a state machine that is comprised of at least a stance state, a swing initiation state, and a swing assist state. In this embodiment, the swing controller is substantially inactive in the stance state and in the swing initiation state, and substantially active in the swing assist state. In one embodiment, the substantially inactive control action in the stance and swing-initiation states is a small amount of emulated damping.

In an exemplary embodiment, the prosthesis controller detects movement between these control states without the need for a load cell that measures ground reaction force. In particular, an important characteristic of the knee prosthesis is low weight and small size. Since a load cell can increase the size, weight, and/or cost of a prosthesis, a preferred embodiment of the PSA includes an IMU on the shank, in addition to a knee angle sensor between the thigh and shank links, rather than a load cell, to detect at least the initiation of or termination of swing phase as described in the following.

Figure 15:
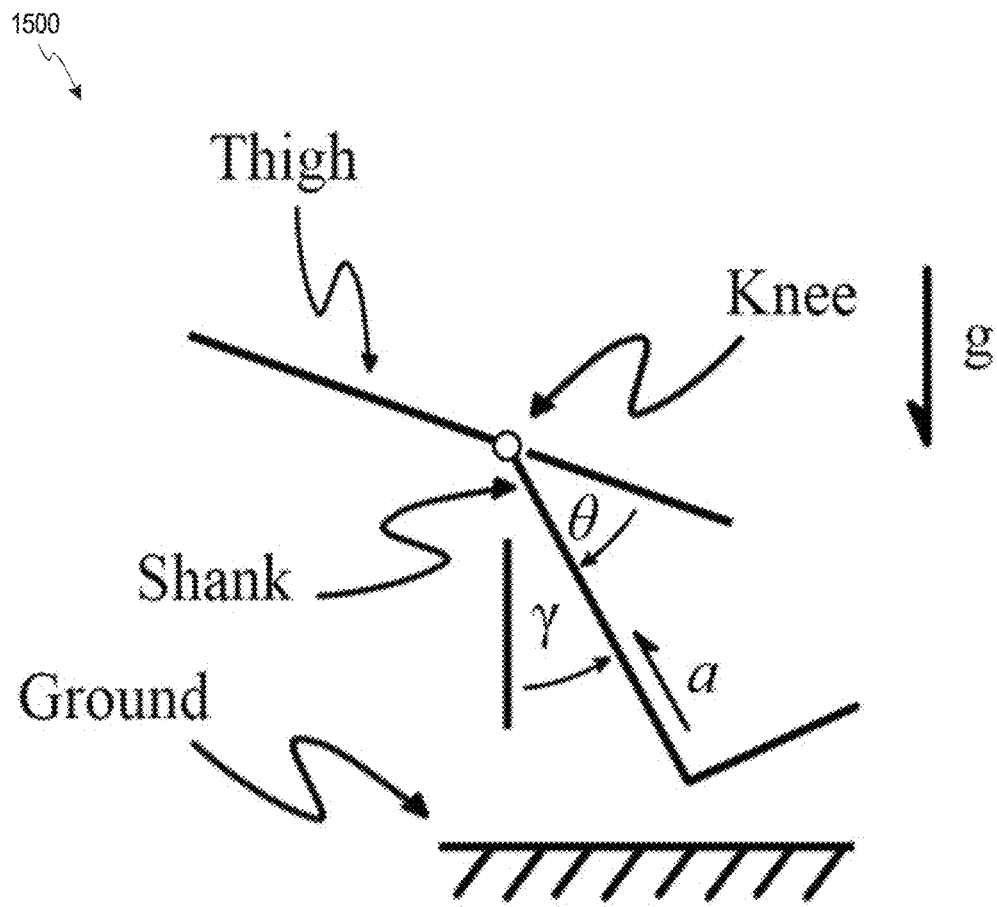
FIG. 15 shows an additional schematic drawing of the geometric conditions that must be satisfied by an exemplary prosthesis, according to the various embodiments.

In an exemplary embodiment, the IMU provides at least the two components of linear acceleration in the sagittal plane, and at least the angular velocity in the sagittal plane, called the shank angular velocity. In a preferred embodiment, these measurements are used to compute the linear acceleration along the long axis of the shank, called the shank axial acceleration, and the angle of the shank with respect to the gravity vector, called the shank angle. The prosthesis also includes angle sensing to measure the angle between the shank link and the thigh link, which is called the knee angle. These measures, and the corresponding signs, are illustrated in FIG. 15.

In an exemplary embodiment, the swing-initiation state is detected based on the following three conditions: 1) the shank axial acceleration is greater than a predetermined threshold; 2) the shank angular velocity is negative; and 3) shank angle is less than a predetermined threshold. Swing is initiated by the user, and as such, while in the swing-initiation state, the swing controller is substantially inactive (i.e., the swing motor is not powered). The swing-initiation is followed by the swing-assist state, which is detected when the knee angle exceeds a predetermined threshold.

When the controller transitions into the swing-assist state, the controller initially executes a real-time generation of a desired trajectory for the swing-assist state. In a preferred embodiment, this trajectory is generated using a cubic spline and is constructed to be substantially representative of the swing-phase knee trajectory of the healthy knee. In this embodiment, the maximum knee flexion angle during swing phase can be selected to be representative of healthy knee motion during swing. In another embodiment, the maximum knee angle during the swing phase can be selected by the user. The maximum knee angle during the swing phase can vary as a function of walking cadence. In all embodiments of a swing-phase trajectory controller, the swing phase trajectory corresponding to the initiation of power-assist swing control is configured to match the knee angle and knee angular velocity at the transition from the swing-initiation state to the swing-assist state.

In an exemplary embodiment, the duration of the swing trajectory is selected as a function of the duration of at least the stance state or the swing-initiation state. In a preferred embodiment, the duration of the swing trajectory is selected as a function of the combined duration of the stance state and the swing-initiation state. In one embodiment, the maximum knee flexion angle during swing is selected as a function of at least the stance state or the swing-initiation state.

Following the real-time generation of the swing trajectory, the swing-assist controller can employ a feedback control law, such as a PD or full-state feedback control law, to minimize the error between the knee angle and the desired knee angle (i.e., the desired trajectory). In a level walking controller, the final knee angle of the desired swing-assist trajectory is the substantially fully-extended configuration. Once the knee angle reaches this substantially fully-extended configuration, and remains in this substantially fully-extended configuration for a predetermined period of time, the controller state machine moves from the swing-assist state to the stance state, and the controller again becomes substantially inactive.

Figure 16:
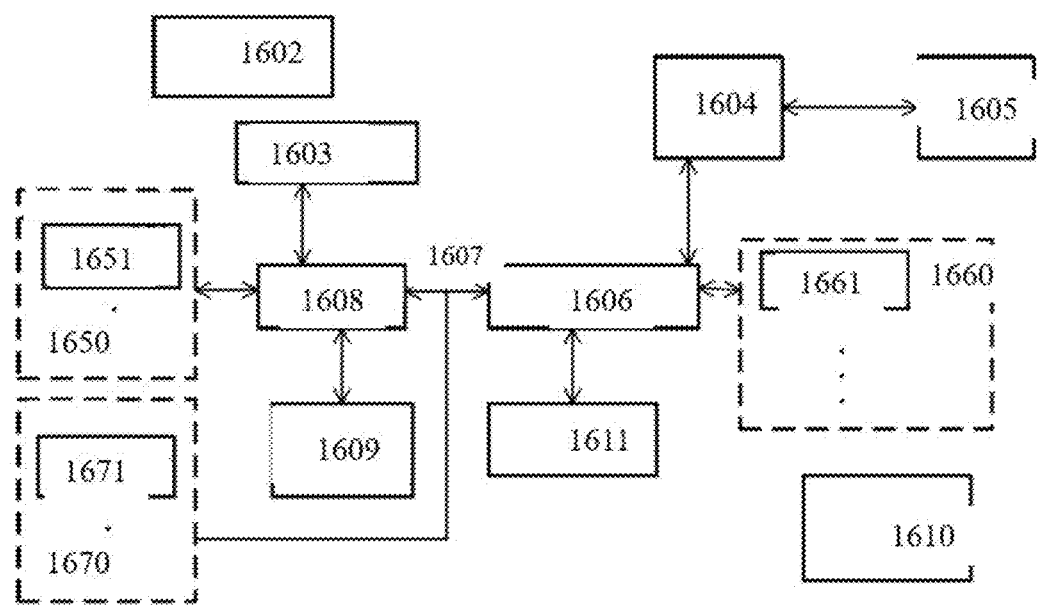
FIG. 16 is a schematic block diagram illustrating an exemplary system, in accordance with an implementation of the present disclosure.

FIG. 16 is a schematic block diagram illustrating an exemplary server system 1600, in accordance with an implementation of the present disclosure. In this example, the server system 1600 includes at least one microprocessor or processor 1604; a BMC 1603; one or more cooling modules 1660; a main memory (MEM) 1611; at least one power supply unit (PSU) 1602 that receives an AC power from an AC power supply 1601, and provides power to various components of the server system 1600, such as the processor 1604, north bridge (NB) logic 1606, PCIe slots 1660, south bridge (SB) logic 1608, storage device 1609, ISA slots 1650, PCI slots 1670, and BMC 1603.

After being powered on, the server system 1600 is configured to load software application from memory, a computer storage device, or an external storage device to perform various operations. The storage device 1609 is structured into logical blocks that are available to an operating system and applications of the server system 1600. The storage device 1609 is configured to retain server data even when the server system 1600 is powered off.

In FIG. 16, the memory 1611 is coupled to the processor 1604 via the NB logic 1606. The memory 1611 may include, but is not limited to, dynamic random access memory (DRAM), double data rate DRAM (DDR DRAM), static RAM (SRAM), or other types of suitable memory. The memory 1611 can be configured to store firmware data of the server system 1600. In some configurations, firmware data can be stored on the storage device 1609.

In some implementations, the server system 1600 can further comprise a flash storage device. The flash storage device can be a flash drive, a random access memory (RAM), a non-volatile random-access memory (NVRAM), or an electrically erasable programmable read-only memory (EEPROM). The flash storage device can be configured to store system configurations such as firmware data.

The processor 1604 can be a central processing unit (CPU) configured to execute program instructions for specific functions. For example, during a booting process, the processor 1604 can access firmware data stored in the BMC 1603 or the flash storage device, and execute the BIOS 1605 to initialize the server system 1600. After the booting process, the processor 1604 can execute an operating system in order to perform and manage specific tasks for the server system 1600.

In some configurations, the processor 1604 can be multi-core processors, each of which is coupled together through a CPU bus connected to the NB logic 1606. In some configurations, the NB logic 1606 can be integrated into the processor 1604. The NB logic 1606 can also be connected to a plurality of peripheral component interconnect express (PCIe) slots 1660 and an SB logic 1608 (optional). The plurality of PCIe slots 1660 can be used for connections and buses such as PCI Express x1, USB 2.0, SMBus, SIM card, future extension for another PCIe lane, 1.5 V and 3.3 V power, and wires to diagnostics LEDs on the server system 1600's chassis.

In system 1600, the NB logic 1606 and the SB logic 1608 are connected by a peripheral component interconnect (PCI) Bus 1607. The PCI Bus 1607 can support functions on the processor 1604 but in a standardized format that is independent of any of the processor 1604's native buses. The PCI Bus 1607 can be further connected to a plurality of PCI slots 1670 (e.g., a PCI slot 1671). Devices connect to the PCI Bus 1607 may appear to a bus controller (not shown) to be connected directly to a CPU bus, assigned addresses in the processor 1604's address space, and synchronized to a single bus clock. PCI cards that can be used in the plurality of PCI slots 1670 include, but are not limited to, network interface cards (NICs), sound cards, modems, TV tuner cards, disk controllers, video cards, small computer system interface (SCSI) adapters, and personal computer memory card international association (PCMCIA) cards.

The SB logic 1608 can couple the PCI Bus 1607 to a plurality of expansion cards or ISA slots 1650 (e.g., an ISA slot 1651) via an expansion bus. The expansion bus can be a bus used for communications between the SB logic 1608 and peripheral devices, and may include, but is not limited to, an industry standard architecture (ISA) bus, PC/1104 bus, low pin count bus, extended ISA (EISA) bus, universal serial bus (USB), integrated drive electronics (IDE) bus, or any other suitable bus that can be used for data communications for peripheral devices.

In this example, BIOS 1605 can be any program instructions or firmware configured to initiate and identify various components of the server system 1600. The BIOS is an important system component that is responsible for initializing and testing hardware components of a corresponding server system. The BIOS can provide an abstraction layer for the hardware components, thereby providing a consistent way for applications and operating systems to interact with a peripheral device such as a keyboard, a display, and other input/output devices.

In system 1600, the SB logic 1608 is further coupled to the BMC 1603 that is connected to the PSU 1602. In some implementations, the BMC 1603 can also be a rack management controller (RMC). The BMC 1603 is configured to monitor operation status of components of the server system 1600, and control the server system 1600 based upon the operation status of the components.

Although only certain components are shown within the exemplary systems 1600 in FIG. 16, various types of electronic or computing components that are capable of processing or storing data, or receiving or transmitting signals, can also be included in the exemplary system 1600. Further, the electronic or computing components in the exemplary system 1600 can be configured to execute various types of application, and/or can use various types of operating systems. These operating systems can include, but are not limited to, Android, Berkeley Software Distribution (BSD), iPhone OS (iOS), Linux, OS X, Unix-like Real-time Operating System (e.g., QNX), Microsoft Windows, Window Phone, and IBM z/OS.

Depending on the desired implementation for the exemplary systems 1600, a variety of networking and messaging protocols can be used, including but not limited to TCP/IP, open systems interconnection (OSI), file transfer protocol (FTP), universal plug and play (UpnP), network file system (NFS), common internet file system (CIFS), AppleTalk etc. As would be appreciated by those skilled in the art, FIG. 16 is used for purposes of explanation. Therefore, a network system can be implemented with many variations, as appropriate, yet still provide a configuration of network platform in accordance with various examples of the present disclosure.

In exemplary configurations of FIG. 16, the exemplary system 1600 can also include one or more wireless components operable to communicate with one or more electronic devices within a computing range of the particular wireless channel. The wireless channel can be any appropriate channel used to enable devices to communicate wirelessly, such as Bluetooth, cellular, NFC, or Wi-Fi channels. It should be understood that the device can have one or more conventional wired communications connections, as known in the art. Various other elements and/or combinations are possible as well within the scope of various examples.

While various examples of the present invention have been described above, it should be understood that they have been presented by way of example only, and not limitation. Numerous changes to the disclosed examples can be made in accordance with the disclosure herein without departing from the spirit or scope of the invention. Thus, the breadth and scope of the present invention should not be limited by any of the above described examples. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular examples only and is not intended to be limiting of the invention. As used herein, the singular forms "a," "an," and "the" are intended to include the plural forms as well, unless the context clearly indicates otherwise. Furthermore, to the extent that the terms "including," "includes," "having," "has," "with," or variants thereof, are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. Furthermore, terms, such as those defined in commonly used dictionaries, should be interpreted as having a meaning that is consistent with their meaning in the context of the relevant art, and will not be interpreted in an idealized or overly formal sense unless expressly so defined herein.

What is claimed is:

1. A knee prosthesis, comprising:
   a shank link;
   a polycentric knee joint comprising an extension stop, the extension stop substantially preventing the knee prosthesis from hyperextending;
   a thigh link rotatably coupled to the shank link by the polycentric knee joint;
   at least one powered control element configured to power rotation of the thigh link relative to the shank link; at least one sensor;
   and a controller coupled to the at least one sensor, the controller configured to:
      receive sensor measurements from the at least one sensor and determine, based at least on the sensor measurements, a present state of a plurality of states comprising at least a swing state and a stance state; and
      cause the at least one powered control element to power rotation if the present state is a swing state;
   wherein the polycentric knee joint is further configured to provide a center of rotation of the thigh link relative to the shank link, wherein the center of rotation is substantially posterior to a ground reaction force vector if the present state is the stance state, and
   wherein the at least one powered control element is configured to apply a maximum torque on the knee prosthesis which is substantially smaller than a maximum torque provided by the polycentric knee joint when the polycentric knee joint is hyperextended.

2. The knee prosthesis of claim 1, wherein the at least one powered control element comprises an electric motor coupled to the thigh link and the shank link through a power screw.

3. The knee prosthesis of claim 2, where the power screw is a backdrivable power screw.

4. The knee prosthesis of claim 1, wherein the at least one powered control element comprises a linear motor drive system configured for power-assisted swing motion assist.

5. The knee prosthesis of claim 1, wherein the at least one powered control element comprises an electric motor coupled rotatably to one of the polycentric mechanism links.

6. The knee prosthesis of claim 1, wherein the polycentric knee joint is a 4-bar knee joint.

7. The knee prosthesis of claim 4, wherein the polycentric knee joint is a 4-bar knee joint, and wherein the polycentric knee and the linear motor drive system comprise a single degree-of-freedom 6-bar mechanism.

8. A knee prosthesis, comprising:
   a shank link;
   a polycentric knee joint comprising an extension stop, the extension stop substantially preventing the knee prosthesis from hyperextending;
   a thigh link rotatably coupled to the shank link by the polycentric knee joint;
   at least one powered control element configured to power rotation of the thigh link relative to the shank link;
   at least one sensor; and
   a controller coupled to the at least one sensor, the controller configured to:
      receive sensor measurements from the at least one sensor and determine, based at least on the sensor measurements, a present state of a plurality of states comprising at least a swing state and a stance state; and
      cause the at least one powered control element to power rotation if the present state is a swing state;
   wherein the polycentric knee joint is further configured to provide a center of rotation of the thigh link relative to the shank link, wherein the center of rotation is substantially posterior to a ground reaction force vector if the present state is the stance state, and
   a plurality of revolute connecting links and a plurality of prismatic connecting links.

9. A knee prosthesis, comprising:
   a shank link;
   a polycentric knee joint comprising an extension stop, the extension stop substantially preventing the knee prosthesis from hyperextending;
   a thigh link rotatably coupled to the shank link by the polycentric knee joint;
   at least one powered control element configured to power rotation of the thigh link relative to the shank link; at least one sensor; and
   a controller coupled to the at least one sensor, the controller configured to:
      receive sensor measurements from the at least one sensor and determine, based at least on the sensor measurements, a present state of a plurality of states comprising at least a swing state and a stance state; and
      cause the at least one powered control element to power rotation if the present state is a swing state;
   wherein the polycentric knee joint is further configured to provide a center of rotation of the thigh link relative to the shank link, wherein the center of rotation is substantially posterior to a ground reaction force vector if the present state is the stance state,
   where the at least one powered control element powers rotation exclusively in the swing state.

* * * * *